United States Patent [19]
Rapp et al.

[11] Patent Number: 5,869,308
[45] Date of Patent: Feb. 9, 1999

[54] DETECTION METHOD FOR C-RAF-1 GENES

[75] Inventors: Ulf R. Rapp, Washington, D.C.; Stephen M. Storm, Frederick, Md.

[73] Assignee: The United States of America as represented by the Department of the Health and Human Services, Washington, D.C.

[21] Appl. No.: 831,317

[22] Filed: Apr. 1, 1997

Related U.S. Application Data

[62] Division of Ser. No. 185,282, Jan. 24, 1994, Pat. No. 5,618,670, which is a continuation of Ser. No. 759,238, Sep. 16, 1991, abandoned, which is a continuation-in-part of Ser. No. 236,947, Aug. 26, 1988, Pat. No. 5,156,841.

[51] Int. Cl.⁶ ............................... C12N 9/12; C07H 21/04
[52] U.S. Cl. .......................... 435/194; 536/23.1; 530/350
[58] Field of Search ........................... 536/23.1; 530/350; 435/194

[56] References Cited

FOREIGN PATENT DOCUMENTS

WO 90/09456 of 0000 WIPO.
WO 91/12343 of 0000 WIPO.
WO91/05064 of 0000 WIPO.

OTHER PUBLICATIONS

Mark et al. "Primary structure of v–raf: relatedness to the src family of oncogenes" Science 224:285–298(1984).

Sutrave et al. "Nucleotide sequence of avian retroviral oncogene v–raf" Nature 309:85–88 (1984).

Bonner, T. I., et al., "The Complete Coding Sequence of the Human raf Oncogene and the Corresponding Structure of the c–raf–I Gene" Chemical Abstracts, vol. 104, No. 19, p. 141, abstract 162785c, (May 12, 1986) and Nucleic Acids Res. 14(2), 1009–15 (1986).

*Primary Examiner*—Stephanie W. Zitomer
*Attorney, Agent, or Firm*—Needle & Rosenberg, P.C.

[57] ABSTRACT

The present invention relates to (1) a method of identifying an individual at an increased risk for developing cancer, (2) a method for determining a prognosis in patients afflicted with cancer, and (3) a method for determining the proper course of treatment for a patient afflicted with cancer; comprising: amplifying a region of the c-raf-1 gene.

8 Claims, 6 Drawing Sheets

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 648 amino acids
        ( B ) TYPE: amino acid
        ( D ) TOPOLOGY: linear ( x i ) SEQUENCE DESCRIPTION: SEQ ID NO:1:

| Met | Glu | His | Ile | Gln | Gly | Ala | Trp | Lys | Thr | Ile | Ser | Asn | Gly | Phe | Gly |
|---|---|---|---|---|---|---|---|---|---|---|---|---|---|---|---|
| 1 | | | | 5 | | | | | 10 | | | | | 15 | |

| Leu | Lys | Asp | Ala | Val | Phe | Asp | Gly | Ser | Ser | Cys | Ile | Ser | Pro | Thr | Ile |
|---|---|---|---|---|---|---|---|---|---|---|---|---|---|---|---|
| | | | 20 | | | | | 25 | | | | | 30 | | |

| Val | Gln | Gln | Phe | Gly | Tyr | Gln | Arg | Arg | Ala | Ser | Asp | Asp | Gly | Lys | Leu |
|---|---|---|---|---|---|---|---|---|---|---|---|---|---|---|---|
| | | 35 | | | | | 40 | | | | | 45 | | | |

| Thr | Asp | Ser | Ser | Lys | Thr | Ser | Asn | Thr | Ile | Arg | Val | Phe | Leu | Pro | Asn |
|---|---|---|---|---|---|---|---|---|---|---|---|---|---|---|---|
| | 50 | | | | | 55 | | | | | 60 | | | | |

| Lys | Gln | Arg | Thr | Val | Val | Asn | Val | Arg | Asn | Gly | Met | Ser | Leu | His | Asp |
|---|---|---|---|---|---|---|---|---|---|---|---|---|---|---|---|
| 65 | | | | | 70 | | | | | 75 | | | | | 80 |

| Cys | Leu | Met | Lys | Ala | Leu | Lys | Val | Arg | Gly | Leu | Gln | Pro | Glu | Cys | Cys |
|---|---|---|---|---|---|---|---|---|---|---|---|---|---|---|---|
| | | | | 85 | | | | | 90 | | | | | 95 | |

| Ala | Val | Phe | Arg | Leu | Leu | Gln | Glu | His | Lys | Gly | Lys | Lys | Ala | Arg | Leu |
|---|---|---|---|---|---|---|---|---|---|---|---|---|---|---|---|
| | | | 100 | | | | | 105 | | | | | 110 | | |

| Asp | Trp | Asn | Thr | Asp | Ala | Ala | Ser | Leu | Ile | Gly | Glu | Glu | Leu | Gln | Val |
|---|---|---|---|---|---|---|---|---|---|---|---|---|---|---|---|
| | | 115 | | | | | 120 | | | | | 125 | | | |

| Asp | Phe | Leu | Asp | His | Val | Pro | Ile | Thr | Thr | His | Asn | Phe | Ala | Arg | Lys |
|---|---|---|---|---|---|---|---|---|---|---|---|---|---|---|---|
| | 130 | | | | | 135 | | | | | 140 | | | | |

| Thr | Phe | Leu | Lys | Leu | Ala | Phe | Cys | Asp | Ile | Cys | Gln | Lys | Phe | Leu | Leu |
|---|---|---|---|---|---|---|---|---|---|---|---|---|---|---|---|
| 145 | | | | | 150 | | | | | 155 | | | | | 160 |

| Asn | Gly | Phe | Arg | Cys | Gln | Thr | Cys | Gly | Tyr | Lys | Phe | His | Glu | His | Cys |
|---|---|---|---|---|---|---|---|---|---|---|---|---|---|---|---|
| | | | | 165 | | | | | 170 | | | | | 175 | |

| Ser | Thr | Lys | Val | Pro | Thr | Met | Cys | Val | Asp | Trp | Ser | Asn | Ile | Arg | Gln |
|---|---|---|---|---|---|---|---|---|---|---|---|---|---|---|---|
| | | | 180 | | | | | 185 | | | | | 190 | | |

| Leu | Leu | Leu | Phe | Pro | Asn | Ser | Thr | Val | Gly | Asp | Ser | Gly | Val | Pro | Ala |
|---|---|---|---|---|---|---|---|---|---|---|---|---|---|---|---|
| | | 195 | | | | | 200 | | | | | 205 | | | |

| Pro | Pro | Ser | Phe | Pro | Met | Arg | Arg | Met | Arg | Glu | Ser | Val | Ser | Arg | Met |
|---|---|---|---|---|---|---|---|---|---|---|---|---|---|---|---|
| | 210 | | | | | 215 | | | | | 220 | | | | |

| Pro | Ala | Ser | Ser | Gln | His | Arg | Tyr | Ser | Thr | Pro | His | Ala | Phe | Thr | Phe |
|---|---|---|---|---|---|---|---|---|---|---|---|---|---|---|---|
| 225 | | | | | 230 | | | | | 235 | | | | | 240 |

| Asn | Thr | Ser | Ser | Pro | Ser | Ser | Glu | Gly | Ser | Leu | Ser | Gln | Arg | Gln | Arg |
|---|---|---|---|---|---|---|---|---|---|---|---|---|---|---|---|
| | | | | 245 | | | | | 250 | | | | | 255 | |

| Ser | Thr | Ser | Thr | Pro | Asn | Val | His | Met | Val | Ser | Thr | Thr | Leu | His | Val |
|---|---|---|---|---|---|---|---|---|---|---|---|---|---|---|---|
| | | | 260 | | | | | 265 | | | | | 270 | | |

| Asp | Ser | Arg | Met | Ile | Glu | Asp | Ala | Ile | Arg | Ser | His | Ser | Glu | Ser | Ala |
|---|---|---|---|---|---|---|---|---|---|---|---|---|---|---|---|
| | | 275 | | | | | 280 | | | | | 285 | | | |

| Ser | Pro | Ser | Ala | Leu | Ser | Ser | Ser | Pro | Asn | Asn | Leu | Ser | Pro | Thr | Gly |
|---|---|---|---|---|---|---|---|---|---|---|---|---|---|---|---|
| | 290 | | | | | 295 | | | | | 300 | | | | |

| Trp | Ser | Gln | Pro | Lys | Thr | Pro | Val | Pro | Ala | Gln | Arg | Glu | Arg | Ala | Pro |
|---|---|---|---|---|---|---|---|---|---|---|---|---|---|---|---|
| 305 | | | | | 310 | | | | | 315 | | | | | 320 |

| Gly | Ser | Gly | Thr | Gln | Gln | Lys | Asn | Lys | Ile | Arg | Pro | Arg | Gly | Gln | Arg |
|---|---|---|---|---|---|---|---|---|---|---|---|---|---|---|---|
| | | | | 325 | | | | | 330 | | | | | 335 | |

| Asp | Ser | Ser | Tyr | Tyr | Trp | Glu | Ile | Glu | Ala | Ser | Glu | Val | Met | Leu | Ser |
|---|---|---|---|---|---|---|---|---|---|---|---|---|---|---|---|
| | | | 340 | | | | | 345 | | | | | 350 | | |

| Thr | Arg | Ile | Gly | Ser | Gly | Ser | Phe | Gly | Thr | Val | Tyr | Lys | Gly | Lys | Trp |
|---|---|---|---|---|---|---|---|---|---|---|---|---|---|---|---|
| | | 355 | | | | | 360 | | | | | 365 | | | |

| His | Gly | Asp | Val | Ala | Val | Lys | Ile | Leu | Lys | Val | Val | Asp | Pro | Thr | Pro |
|---|---|---|---|---|---|---|---|---|---|---|---|---|---|---|---|
| | 370 | | | | | 375 | | | | | 380 | | | | |

| Glu | Gln | Leu | Gln | Ala | Phe | Arg | Asn | Glu | Val | Ala | Val | Leu | Arg | Lys | Thr |
|---|---|---|---|---|---|---|---|---|---|---|---|---|---|---|---|
| 385 | | | | | 390 | | | | | 395 | | | | | 400 |

| Arg | His | Val | Asn | Ile | Leu | Leu | Phe | Met | Gly | Tyr | Met | Thr | Lys | Asp | Asn |
|---|---|---|---|---|---|---|---|---|---|---|---|---|---|---|---|
| | | | | 405 | | | | | 410 | | | | | 415 | |

Leu  Ala  Ile  Val  Thr  Gln  Trp  Cys  Glu  Gly  Ser  Ser  Leu  Tyr  Lys  His
                               420                 425                           430

Leu  His  Val  Gln  Glu  Thr  Lys  Phe  Gln  Met  Phe  Gln  Leu  Ile  Asp  Ile
                          435                 440                      445

Ala  Arg  Gln  Thr  Ala  Gln  Gly  Met  Asp  Tyr  Leu  His  Ala  Lys  Asn  Ile
                     450                 455                      460

Ile  His  Arg  Asp  Met  Lys  Ser  Asn  Asn  Ile  Phe  Leu  His  Glu  Gly  Leu
                465                      470                      475                           480

Thr  Val  Lys  Ile  Gly  Asp  Phe  Gly  Leu  Ala  Thr  Val  Lys  Ser  Arg  Trp
                               485                           490                      495

Ser  Gly  Ser  Gln  Gln  Val  Glu  Gln  Pro  Thr  Gly  Ser  Val  Leu  Trp  Met
                               500                 505                           510

Ala  Pro  Glu  Val  Ile  Arg  Met  Gln  Asp  Asp  Asn  Pro  Phe  Ser  Phe  Gln
                          515                      520                      525

Ser  Asp  Val  Tyr  Ser  Tyr  Gly  Ile  Val  Leu  Tyr  Glu  Leu  Met  Ala  Gly
                     530                      535                      540

Glu  Leu  Pro  Tyr  Ala  His  Ile  Asn  Asn  Arg  Asp  Gln  Ile  Ile  Phe  Met
                545                      550                      555                           560

Val  Gly  Arg  Gly  Tyr  Ala  Ser  Pro  Asp  Leu  Ser  Arg  Leu  Tyr  Lys  Asn
                               565                      570                      575

Cys  Pro  Lys  Ala  Met  Lys  Arg  Leu  Val  Ala  Asp  Cys  Val  Lys  Lys  Val
                          580                      585                      590

Lys  Glu  Glu  Arg  Pro  Leu  Phe  Pro  Gln  Ile  Leu  Ser  Ser  Ile  Glu  Leu
                          595                      600                      605

Leu  Gln  His  Ser  Leu  Pro  Lys  Ile  Asn  Arg  Ser  Ala  Ser  Glu  Pro  Ser
                     610                      615                      620

Leu  His  Arg  Ala  Ala  His  Thr  Glu  Asp  Ile  Asn  Ala  Cys  Thr  Leu  Thr
                625                      630                      635                           640

Thr  Ser  Pro  Arg  Leu  Pro  Val  Phe
                               645

( 2 ) INFORMATION FOR SEQ ID NO:2:

( i ) SEQUENCE CHARACTERISTICS:
            ( A ) LENGTH: 648 amino acids
            ( B ) TYPE: amino acid
            ( D ) TOPOLOGY: linear ( x i ) SEQUENCE DESCRIPTION: SEQ ID NO:2:

Met  Glu  His  Ile  Gln  Gly  Ala  Trp  Lys  Thr  Ile  Ser  Asn  Gly  Phe  Gly
                1                   5                   10                          15

Leu  Lys  Asp  Ala  Val  Phe  Asp  Gly  Ser  Ser  Cys  Ile  Ser  Pro  Thr  Ile
                               20                  25                           30

Val  Gln  Gln  Phe  Gly  Tyr  Gln  Arg  Arg  Ala  Ser  Asp  Asp  Gly  Lys  Leu
                          35                  40                       45

Thr  Asp  Ser  Ser  Lys  Thr  Ser  Asn  Thr  Ile  Arg  Val  Phe  Leu  Pro  Asn
                     50                       55                      60

Lys  Gln  Arg  Thr  Val  Val  Asn  Val  Arg  Asn  Gly  Met  Ser  Leu  His  Asp
                65                       70                      75                            80

Cys  Leu  Met  Lys  Ala  Leu  Lys  Val  Arg  Gly  Leu  Gln  Pro  Glu  Cys  Cys
                               85                       90                          95

Ala  Val  Phe  Arg  Leu  Leu  Gln  Glu  His  Lys  Gly  Lys  Lys  Ala  Arg  Leu
                          100                      105                     110

Asp  Trp  Asn  Thr  Asp  Ala  Ala  Ser  Leu  Ile  Gly  Glu  Glu  Leu  Gln  Val
                          115                      120                     125

| | | | | | | | | | | | | |
|---|---|---|---|---|---|---|---|---|---|---|---|---|
|Asp|Phe|Leu|Asp|His|Val|Pro|Ile|Thr|Thr|His|Asn|Phe|Ala|Arg|Lys|
| |130| | | |135| | | | |140| | | | | |

Thr Phe Leu Lys Leu Ala Phe Cys Asp Ile Cys Gln Lys Phe Leu Leu
145             150             155                 160

Asn Gly Phe Arg Cys Gln Thr Cys Gly Tyr Lys Phe His Glu His Cys
                165             170                 175

Ser Thr Lys Val Pro Thr Met Cys Val Asp Trp Ser Asn Ile Arg Gln
            180             185                 190

Leu Leu Leu Phe Pro Asn Ser Thr Val Gly Asp Ser Gly Val Pro Ala
                195             200             205

Pro Pro Ser Phe Pro Met Arg Arg Met Arg Glu Ser Val Ser Arg Met
    210             215                 220

Pro Ala Ser Ser Gln His Arg Tyr Ser Thr Pro His Ala Phe Thr Phe
225             230                 235                         240

Asn Thr Ser Ser Pro Ser Ser Glu Gly Ser Leu Ser Gln Arg Gln Arg
                245             250                 255

Ser Thr Ser Thr Pro Asn Val His Met Val Ser Thr Thr Leu His Val
            260             265                 270

Asp Ser Arg Met Ile Glu Asp Ala Ile Arg Ser His Ser Glu Ser Ala
        275             280                 285

Ser Pro Ser Ala Leu Ser Ser Ser Pro Asn Asn Leu Ser Pro Thr Gly
    290             295                 300

Trp Ser Gln Pro Lys Thr Pro Val Pro Ala Gln Arg Glu Arg Ala Pro
305             310                 315                         320

Gly Ser Gly Thr Gln Gln Lys Asn Lys Ile Arg Pro Arg Gly Gln Arg
                325             330                 335

Asp Ser Ser Tyr Tyr Trp Glu Ile Glu Ala Ser Glu Val Met Leu Ser
            340             345                 350

Thr Arg Ile Gly Ser Gly Ser Phe Gly Thr Val Tyr Lys Gly Lys Trp
        355             360                 365

His Gly Asp Val Ala Val Lys Ile Leu Lys Val Val Asp Pro Thr Pro
    370             375                 380

Glu Gln Leu Gln Ala Phe Arg Asn Glu Val Ala Val Leu Arg Lys Thr
385             390                 395                         400

Arg His Val Asn Ile Leu Leu Phe Met Gly Tyr Met Thr Lys Asp Asn
                405             410                 415

Leu Ala Ile Val Thr Gln Trp Cys Glu Gly Ser Ser Leu Tyr Lys His
            420             425                 430

Leu His Val Gln Glu Thr Lys Phe Gln Met Phe Gln Leu Ile Asp Ile
        435             440                 445

Ala Arg Gln Thr Ala Gln Gly Met Asp Tyr Leu His Ala Lys Asn Ile
    450             455                 460

Ile His Arg Asp Met Lys Ser Asn Asn Ile Phe Leu His Glu Gly Leu
465             470                 475                         480

Thr Val Lys Ile Gly Asp Phe Gly Leu Ala Thr Val Lys Ser Arg Trp
                485             490                 495

Ser Gly Ser Gln Gln Val Glu Gln Pro Thr Gly Ser Val Leu Trp Met
            500             505                 510

Ala Pro Glu Val Val Arg Met Gln Asp Asn Pro Phe Ser Phe Gln
        515             520                 525

Ser Asp Val Tyr Ser Tyr Gly Ile Val Leu Tyr Glu Leu Met Ala Gly
    530             535                 540

Glu Leu Pro Tyr Ala His Ile Asn Asn Arg Asp Gln Ile Ile Phe Met
545             550                 555                         560

```
Val  Gly  Arg  Gly  Tyr  Ala  Ser  Pro  Asp  Leu  Ser  Arg  Leu  Tyr  Lys  Asn
               565                      570                      575

Cys  Pro  Lys  Ala  Met  Lys  Arg  Leu  Val  Ala  Asp  Cys  Val  Lys  Lys  Val
               580                      585                      590

Lys  Glu  Glu  Arg  Pro  Leu  Phe  Pro  Gln  Ile  Leu  Ser  Ser  Ile  Glu  Leu
          595                      600                      605

Leu  Gln  His  Ser  Leu  Pro  Lys  Ile  Asn  Arg  Ser  Ala  Ser  Glu  Pro  Ser
          610                      615                      620

Leu  His  Arg  Ala  Ala  His  Thr  Glu  Asp  Ile  Asn  Ala  Cys  Thr  Leu  Thr
625                      630                      635                      640

Thr  Ser  Pro  Arg  Leu  Pro  Val  Phe
               645
```

( 2 ) INFORMATION FOR SEQ ID NO:3:

( i ) SEQUENCE CHARACTERISTICS:
        ( A ) LENGTH: 648 amino acids
        ( B ) TYPE: amino acid
        ( D ) TOPOLOGY: linear ( x i ) SEQUENCE DESCRIPTION: SEQ ID NO:3:

```
Met  Glu  His  Ile  Gln  Gly  Ala  Trp  Lys  Thr  Ile  Ser  Asn  Gly  Phe  Gly
1                   5                        10                      15

Leu  Lys  Asp  Ala  Val  Phe  Asp  Gly  Ser  Ser  Cys  Ile  Ser  Pro  Thr  Ile
               20                      25                      30

Val  Gln  Gln  Phe  Gly  Tyr  Gln  Arg  Arg  Ala  Ser  Asp  Gly  Lys  Leu
          35                      40                      45

Thr  Asp  Ser  Ser  Lys  Thr  Ser  Asn  Thr  Ile  Arg  Val  Phe  Leu  Pro  Asn
     50                      55                      60

Lys  Gln  Arg  Thr  Val  Val  Asn  Val  Arg  Asn  Gly  Met  Ser  Leu  His  Asp
65                       70                      75                       80

Cys  Leu  Met  Lys  Ala  Leu  Lys  Val  Arg  Gly  Leu  Gln  Pro  Glu  Cys  Cys
               85                      90                       95

Ala  Val  Phe  Arg  Leu  Leu  Gln  Glu  His  Lys  Gly  Lys  Lys  Ala  Arg  Leu
               100                     105                     110

Asp  Trp  Asn  Thr  Asp  Ala  Ala  Ser  Leu  Ile  Gly  Glu  Glu  Leu  Gln  Val
          115                     120                     125

Asp  Phe  Leu  Asp  His  Val  Pro  Ile  Thr  Thr  His  Asn  Phe  Ala  Arg  Lys
     130                     135                     140

Thr  Phe  Leu  Lys  Leu  Ala  Phe  Cys  Asp  Ile  Cys  Gln  Lys  Phe  Leu  Leu
145                      150                     155                      160

Asn  Gly  Phe  Arg  Cys  Gln  Thr  Cys  Gly  Tyr  Lys  Phe  His  Glu  His  Cys
               165                     170                     175

Ser  Thr  Lys  Val  Pro  Thr  Met  Cys  Val  Asp  Trp  Ser  Asn  Ile  Arg  Gln
               180                     185                     190

Leu  Leu  Leu  Phe  Pro  Asn  Ser  Thr  Val  Gly  Asp  Ser  Gly  Val  Pro  Ala
          195                     200                     205

Pro  Pro  Ser  Phe  Pro  Met  Arg  Arg  Met  Arg  Glu  Ser  Val  Ser  Arg  Met
     210                     215                     220

Pro  Ala  Ser  Ser  Gln  His  Arg  Tyr  Ser  Thr  Pro  His  Ala  Phe  Thr  Phe
225                      230                     235                      240

Asn  Thr  Ser  Ser  Pro  Ser  Ser  Glu  Gly  Ser  Leu  Ser  Gln  Arg  Gln  Arg
               245                     250                     255

Ser  Thr  Ser  Thr  Pro  Asn  Val  His  Met  Val  Ser  Thr  Thr  Leu  His  Val
               260                     265                     270
```

```
Asp  Ser  Arg  Met  Ile  Glu  Asp  Ala  Ile  Arg  Ser  His  Ser  Glu  Ser  Ala
          275                 280                 285

Ser  Pro  Ser  Ala  Leu  Ser  Ser  Pro  Asn  Asn  Leu  Ser  Pro  Thr  Gly
     290                 295                 300

Trp  Ser  Gln  Pro  Lys  Thr  Pro  Val  Pro  Ala  Gln  Arg  Glu  Arg  Ala  Pro
305                      310                 315                           320

Gly  Ser  Gly  Thr  Gln  Gln  Lys  Asn  Lys  Ile  Arg  Pro  Arg  Gly  Gln  Arg
               325                      330                      335

Asp  Ser  Ser  Tyr  Tyr  Trp  Glu  Ile  Glu  Ala  Ser  Glu  Val  Met  Leu  Ser
               340                 345                      350

Thr  Arg  Ile  Gly  Ser  Gly  Ser  Phe  Gly  Thr  Val  Tyr  Lys  Gly  Lys  Trp
          355                 360                      365

His  Gly  Asp  Val  Ala  Val  Lys  Ile  Leu  Lys  Val  Val  Asp  Pro  Thr  Pro
     370                 375                      380

Glu  Gln  Leu  Gln  Ala  Phe  Arg  Asn  Glu  Val  Ala  Val  Leu  Arg  Lys  Thr
385                      390                 395                           400

Arg  His  Val  Asn  Ile  Leu  Leu  Phe  Met  Gly  Tyr  Met  Thr  Lys  Asp  Asn
               405                 410                           415

Leu  Ala  Ile  Val  Thr  Gln  Trp  Cys  Glu  Gly  Ser  Ser  Leu  Tyr  Lys  His
               420                 425                      430

Leu  His  Val  Gln  Glu  Thr  Lys  Phe  Gln  Met  Phe  Gln  Leu  Ile  Asp  Ile
          435                 440                      445

Ala  Arg  Gln  Thr  Ala  Gln  Gly  Met  Asp  Tyr  Leu  His  Ala  Lys  Asn  Ile
     450                 455                      460

Ile  His  Arg  Asp  Met  Lys  Ser  Asn  Asn  Ile  Phe  Leu  His  Glu  Gly  Leu
465                      470                 475                           480

Thr  Val  Lys  Ile  Gly  Asp  Phe  Gly  Leu  Ala  Thr  Val  Lys  Ser  Arg  Trp
               485                 490                      495

Ser  Gly  Ser  Gln  Gln  Val  Glu  Gln  Pro  Thr  Gly  Ser  Val  Leu  Trp  Met
               500                 505                      510

Ala  Pro  Glu  Val  Ile  Arg  Met  Gln  Asp  Asn  Asn  Pro  Phe  Ser  Phe  Gln
          515                 520                      525

Ser  Asp  Val  Tyr  Ser  Tyr  Gly  Ile  Val  Leu  Tyr  Glu  Leu  Met  Ala  Gly
     530                 535                      540

Glu  Leu  Pro  Tyr  Ala  His  Ile  Asn  Asn  Arg  Asp  Gln  Ile  Ile  Phe  Met
545                      550                 555                           560

Val  Gly  Arg  Gly  Tyr  Ala  Ser  Pro  Asp  Leu  Ser  Arg  Leu  Tyr  Lys  Asn
               565                 570                      575

Cys  Pro  Lys  Ala  Met  Lys  Arg  Leu  Val  Ala  Asp  Cys  Val  Lys  Lys  Val
               580                 585                      590

Lys  Glu  Glu  Arg  Pro  Leu  Phe  Pro  Gln  Ile  Leu  Ser  Ser  Ile  Glu  Leu
          595                 600                      605

Leu  Gln  His  Ser  Leu  Pro  Lys  Ile  Asn  Arg  Ser  Ala  Ser  Glu  Pro  Ser
     610                 615                      620

Leu  His  Arg  Ala  Ala  His  Thr  Glu  Asp  Ile  Asn  Ala  Cys  Thr  Leu  Thr
625                      630                 635                           640

Thr  Ser  Pro  Arg  Leu  Pro  Val  Phe
               645
```

( 2 ) INFORMATION FOR SEQ ID NO:4:

( i ) SEQUENCE CHARACTERISTICS:
        ( A ) LENGTH: 648 amino acids
        ( B ) TYPE: amino acid
        ( D ) TOPOLOGY: linear ( x i ) SEQUENCE DESCRIPTION: SEQ ID NO:4:

| Met<br>1 | Glu | His | Ile | Gln<br>5 | Gly | Ala | Trp | Lys | Thr<br>10 | Ile | Ser | Asn | Gly | Phe<br>15 | Gly |
|---|---|---|---|---|---|---|---|---|---|---|---|---|---|---|---|
| Leu | Lys | Asp | Ala<br>20 | Val | Phe | Asp | Gly | Ser<br>25 | Ser | Cys | Ile | Ser | Pro<br>30 | Thr | Ile |
| Val | Gln | Gln<br>35 | Phe | Gly | Tyr | Gln | Arg<br>40 | Arg | Ala | Ser | Asp | Asp<br>45 | Gly | Lys | Leu |
| Thr | Asp<br>50 | Ser | Ser | Lys | Thr | Ser<br>55 | Asn | Thr | Ile | Arg | Val<br>60 | Phe | Leu | Pro | Asn |
| Lys<br>65 | Gln | Arg | Thr | Val | Val<br>70 | Asn | Val | Arg | Asn | Gly<br>75 | Met | Ser | Leu | His | Asp<br>80 |
| Cys | Leu | Met | Lys | Ala<br>85 | Leu | Lys | Val | Arg | Gly<br>90 | Leu | Gln | Pro | Glu | Cys<br>95 | Cys |
| Ala | Val | Phe | Arg<br>100 | Leu | Leu | Gln | Glu | His<br>105 | Lys | Gly | Lys | Lys | Ala<br>110 | Arg | Leu |
| Asp | Trp | Asn<br>115 | Thr | Asp | Ala | Ala | Ser<br>120 | Leu | Ile | Gly | Glu | Glu<br>125 | Leu | Gln | Val |
| Asp | Phe<br>130 | Leu | Asp | His | Val | Pro<br>135 | Ile | Thr | Thr | His | Asn<br>140 | Phe | Ala | Arg | Lys |
| Thr<br>145 | Phe | Leu | Lys | Leu | Ala<br>150 | Phe | Cys | Asp | Ile | Cys<br>155 | Gln | Lys | Phe | Leu | Leu<br>160 |
| Asn | Gly | Phe | Arg | Cys<br>165 | Gln | Thr | Cys | Gly | Tyr<br>170 | Lys | Phe | His | Glu | His<br>175 | Cys |
| Ser | Thr | Lys | Val<br>180 | Pro | Thr | Met | Cys | Val<br>185 | Asp | Trp | Ser | Asn | Ile<br>190 | Arg | Gln |
| Leu | Leu | Leu<br>195 | Phe | Pro | Asn | Ser | Thr<br>200 | Val | Gly | Asp | Ser | Gly<br>205 | Val | Pro | Ala |
| Pro | Pro<br>210 | Ser | Phe | Pro | Met | Arg<br>215 | Arg | Met | Arg | Glu | Ser<br>220 | Val | Ser | Arg | Met |
| Pro<br>225 | Ala | Ser | Ser | Gln | His<br>230 | Arg | Tyr | Ser | Thr | Pro<br>235 | His | Ala | Phe | Thr | Phe<br>240 |
| Asn | Thr | Ser | Ser | Pro<br>245 | Ser | Ser | Glu | Gly | Ser<br>250 | Leu | Ser | Gln | Arg | Gln<br>255 | Arg |
| Ser | Thr | Ser | Thr<br>260 | Pro | Asn | Val | His | Met<br>265 | Val | Ser | Thr | Thr | Leu<br>270 | His | Val |
| Asp | Ser | Arg<br>275 | Met | Ile | Glu | Asp | Ala<br>280 | Ile | Arg | Ser | His | Ser<br>285 | Glu | Ser | Ala |
| Ser | Pro<br>290 | Ser | Ala | Leu | Ser | Ser<br>295 | Ser | Pro | Asn | Asn | Leu<br>300 | Ser | Pro | Thr | Gly |
| Trp<br>305 | Ser | Gln | Pro | Lys | Thr<br>310 | Pro | Val | Pro | Ala | Gln<br>315 | Arg | Glu | Arg | Ala | Pro<br>320 |
| Gly | Ser | Gly | Thr | Gln<br>325 | Gln | Lys | Asn | Lys | Ile<br>330 | Arg | Pro | Arg | Gly | Gln<br>335 | Arg |
| Asp | Ser | Ser | Tyr<br>340 | Tyr | Trp | Glu | Ile | Glu<br>345 | Ala | Ser | Glu | Val | Met<br>350 | Leu | Ser |
| Thr | Arg | Ile<br>355 | Gly | Ser | Gly | Ser | Phe<br>360 | Gly | Thr | Val | Tyr | Lys<br>365 | Gly | Lys | Trp |
| His | Gly<br>370 | Asp | Val | Ala | Val | Lys<br>375 | Ile | Leu | Lys | Val | Val<br>380 | Asp | Pro | Thr | Pro |
| Glu<br>385 | Gln | Leu | Gln | Ala | Phe<br>390 | Arg | Asn | Glu | Val | Ala<br>395 | Val | Leu | Arg | Lys | Thr<br>400 |
| Arg | His | Val | Asn | Ile<br>405 | Leu | Leu | Phe | Met | Gly<br>410 | Tyr | Met | Thr | Lys | Asp<br>415 | Asn |

| | | | | | | | | | | | | | | |
|---|---|---|---|---|---|---|---|---|---|---|---|---|---|---|
| Leu | Ala | Ile | Val 420 | Thr | Gln | Trp | Cys | Glu 425 | Gly | Ser | Ser | Leu | Tyr 430 | Lys | His |
| Leu | His | Val 435 | Gln | Glu | Thr | Lys | Phe 440 | Gln | Met | Phe | Gln | Leu 445 | Ile | Asp | Ile |
| Ala | Arg 450 | Gln | Thr | Ala | Gln | Gly 455 | Met | Asp | Tyr | Leu | His 460 | Ala | Lys | Asn | Ile |
| Ile 465 | His | Arg | Asp | Met | Lys 470 | Ser | Asn | Asn | Ile | Phe 475 | Leu | His | Glu | Gly | Leu 480 |
| Thr | Val | Lys | Ile | Gly 485 | Asp | Phe | Gly | Leu | Ala 490 | Thr | Val | Lys | Ser | Arg 495 | Trp |
| Ser | Gly | Ser | Gln 500 | Gln | Val | Glu | Gln | Pro 505 | Thr | Gly | Ser | Val | Leu 510 | Trp | Met |
| Ala | Pro | Glu 515 | Val | Ile | Arg | Met | Gln 520 | Asp | Asp | Asn | Pro | Phe 525 | Ser | Ser | Gln |
| Ser | Asp 530 | Val | Tyr | Ser | Tyr | Gly 535 | Ile | Val | Leu | Tyr | Glu 540 | Leu | Met | Ala | Gly |
| Glu 545 | Leu | Pro | Tyr | Ala | His 550 | Ile | Asn | Asn | Arg | Asp 555 | Gln | Ile | Ile | Phe | Met 560 |
| Val | Gly | Arg | Gly | Tyr 565 | Ala | Ser | Pro | Asp | Leu 570 | Ser | Arg | Leu | Tyr | Lys 575 | Asn |
| Cys | Pro | Lys | Ala 580 | Met | Lys | Arg | Leu | Val 585 | Ala | Asp | Cys | Val | Lys 590 | Lys | Val |
| Lys | Glu | Glu 595 | Arg | Pro | Leu | Phe | Pro 600 | Gln | Ile | Leu | Ser | Ser 605 | Ile | Glu | Leu |
| Leu | Gln 610 | His | Ser | Leu | Pro | Lys 615 | Ile | Asn | Arg | Ser | Ala 620 | Ser | Glu | Pro | Ser |
| Leu 625 | His | Arg | Ala | Ala | His 630 | Thr | Glu | Asp | Ile | Asn 635 | Ala | Cys | Thr | Leu | Thr 640 |
| Thr | Ser | Pro | Arg | Leu 645 | Pro | Val | Phe | | | | | | | | |

(2) INFORMATION FOR SEQ ID NO:5:

(i) SEQUENCE CHARACTERISTICS:
    (A) LENGTH: 648 amino acids
    (B) TYPE: amino acid
    (D) TOPOLOGY: linear (xi) SEQUENCE DESCRIPTION: SEQ ID NO:5:

| | | | | | | | | | | | | | | |
|---|---|---|---|---|---|---|---|---|---|---|---|---|---|---|
| Met 1 | Glu | His | Ile | Gln 5 | Gly | Ala | Trp | Lys | Thr 10 | Ile | Ser | Asn | Gly | Phe 15 | Gly |
| Leu | Lys | Asp | Ala 20 | Val | Phe | Asp | Gly | Ser 25 | Ser | Cys | Ile | Ser | Pro 30 | Thr | Ile |
| Val | Gln | Gln 35 | Phe | Gly | Tyr | Gln | Arg 40 | Arg | Ala | Ser | Asp | Asp 45 | Gly | Lys | Leu |
| Thr | Asp 50 | Ser | Ser | Lys | Thr | Ser 55 | Asn | Thr | Ile | Arg | Val 60 | Phe | Leu | Pro | Asn |
| Lys 65 | Gln | Arg | Thr | Val | Val 70 | Asn | Val | Arg | Asn | Gly 75 | Met | Ser | Leu | His | Asp 80 |
| Cys | Leu | Met | Lys | Ala 85 | Leu | Lys | Val | Arg | Gly 90 | Leu | Gln | Pro | Glu | Cys 95 | Cys |
| Ala | Val | Phe | Arg 100 | Leu | Leu | Gln | Glu | His 105 | Lys | Gly | Lys | Lys | Ala 110 | Arg | Leu |
| Asp | Trp | Asn 115 | Thr | Asp | Ala | Ala | Ser 120 | Leu | Ile | Gly | Glu | Glu 125 | Leu | Gln | Val |

```
Asp  Phe  Leu  Asp  His  Val  Pro  Ile  Thr  Thr  His  Asn  Phe  Ala  Arg  Lys
     130                 135                      140

Thr  Phe  Leu  Lys  Leu  Ala  Phe  Cys  Asp  Ile  Cys  Gln  Lys  Phe  Leu  Leu
145                      150                 155                           160

Asn  Gly  Phe  Arg  Cys  Gln  Thr  Cys  Gly  Tyr  Lys  Phe  His  Glu  His  Cys
                    165                      170                      175

Ser  Thr  Lys  Val  Pro  Thr  Met  Cys  Val  Asp  Trp  Ser  Asn  Ile  Arg  Gln
               180                 185                      190

Leu  Leu  Leu  Phe  Pro  Asn  Ser  Thr  Val  Gly  Asp  Ser  Gly  Val  Pro  Ala
          195                      200                 205

Pro  Pro  Ser  Phe  Pro  Met  Arg  Arg  Met  Arg  Glu  Ser  Val  Ser  Arg  Met
     210                      215                 220

Pro  Ala  Ser  Ser  Gln  His  Arg  Tyr  Ser  Thr  Pro  His  Ala  Phe  Thr  Phe
225                      230                      235                      240

Asn  Thr  Ser  Ser  Pro  Ser  Ser  Glu  Gly  Ser  Leu  Ser  Gln  Arg  Gln  Arg
                    245                      250                      255

Ser  Thr  Ser  Thr  Pro  Asn  Val  His  Met  Val  Ser  Thr  Thr  Leu  His  Val
               260                 265                      270

Asp  Ser  Arg  Met  Ile  Glu  Asp  Ala  Ile  Arg  Ser  His  Ser  Glu  Ser  Ala
               275                 280                 285

Ser  Pro  Ser  Ala  Leu  Ser  Ser  Ser  Pro  Asn  Asn  Leu  Ser  Pro  Thr  Gly
     290                      295                 300

Trp  Ser  Gln  Pro  Lys  Thr  Pro  Val  Pro  Ala  Gln  Arg  Glu  Arg  Ala  Pro
305                      310                 315                           320

Gly  Ser  Gly  Thr  Gln  Gln  Lys  Asn  Lys  Ile  Arg  Pro  Arg  Gly  Gln  Arg
                    325                      330                      335

Asp  Ser  Ser  Tyr  Tyr  Trp  Glu  Ile  Glu  Ala  Ser  Glu  Val  Met  Leu  Ser
               340                      345                 350

Thr  Arg  Ile  Gly  Ser  Gly  Ser  Phe  Gly  Thr  Val  Tyr  Lys  Gly  Lys  Trp
               355                      360                 365

His  Gly  Asp  Val  Ala  Val  Lys  Ile  Leu  Lys  Val  Val  Asp  Pro  Thr  Pro
     370                      375                 380

Glu  Gln  Leu  Gln  Ala  Phe  Arg  Asn  Glu  Val  Ala  Val  Leu  Arg  Lys  Thr
385                      390                 395                           400

Arg  His  Val  Asn  Ile  Leu  Leu  Phe  Met  Gly  Tyr  Met  Thr  Lys  Asp  Asn
                    405                      410                      415

Leu  Ala  Ile  Val  Thr  Gln  Trp  Cys  Glu  Gly  Ser  Ser  Leu  Tyr  Lys  His
               420                 425                      430

Leu  His  Val  Gln  Glu  Thr  Lys  Phe  Gln  Met  Phe  Gln  Leu  Ile  Asp  Ile
     435                      440                 445

Ala  Arg  Gln  Thr  Ala  Gln  Gly  Met  Asp  Tyr  Leu  His  Ala  Lys  Asn  Ile
     450                      455                 460

Ile  His  Arg  Asp  Met  Lys  Ser  Asn  Asn  Ile  Phe  Leu  His  Glu  Gly  Leu
465                      470                      475                      480

Thr  Val  Lys  Ile  Gly  Asp  Phe  Gly  Leu  Ala  Thr  Val  Lys  Ser  Arg  Trp
               485                      490                      495

Ser  Gly  Ser  Gln  Gln  Val  Glu  Gln  Pro  Thr  Gly  Ser  Val  Leu  Trp  Met
               500                      505                      510

Ala  Pro  Glu  Val  Ile  Arg  Met  Gln  Asp  Asn  Pro  Phe  Ser  Phe  Gln
     515                      520                      525

Ser  Thr  Cys  Thr  Phe  Tyr  Gly  Ile  Val  Leu  Tyr  Glu  Leu  Met  Ala  Gly
          530                      535                 540

Glu  Leu  Pro  Tyr  Ala  His  Ile  Asn  Asn  Arg  Asp  Gln  Ile  Ile  Phe  Met
545                      550                      555                      560
```

|  |  |  |  |  |  |  |  |  |  |  |  |  |  |  |
|--|--|--|--|--|--|--|--|--|--|--|--|--|--|--|
| Val | Gly | Arg | Gly | Tyr | Ala | Ser | Pro | Asp | Leu | Ser | Arg | Leu | Tyr | Lys | Asn |
|  |  |  |  | 565 |  |  |  | 570 |  |  |  |  | 575 |  |
| Cys | Pro | Lys | Ala | Met | Lys | Arg | Leu | Val | Ala | Asp | Cys | Val | Lys | Lys | Val |
|  |  |  | 580 |  |  |  | 585 |  |  |  |  | 590 |  |  |
| Lys | Glu | Glu | Arg | Pro | Leu | Phe | Pro | Gln | Ile | Leu | Ser | Ser | Ile | Glu | Leu |
|  |  | 595 |  |  |  |  | 600 |  |  |  |  | 605 |  |  |  |
| Leu | Gln | His | Ser | Leu | Pro | Lys | Ile | Asn | Arg | Ser | Ala | Ser | Glu | Pro | Ser |
|  | 610 |  |  |  |  | 615 |  |  |  |  | 620 |  |  |  |  |
| Leu | His | Arg | Ala | Ala | His | Thr | Glu | Asp | Ile | Asn | Ala | Cys | Thr | Leu | Thr |
| 625 |  |  |  |  | 630 |  |  |  |  | 635 |  |  |  |  | 640 |
| Thr | Ser | Pro | Arg | Leu | Pro | Val | Phe |
|  |  |  |  | 645 |  |  |  |

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

AACTTGTGGT GGTTGGACCT                                                                20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TCATCCACAA AGTGATTCTG                                                              20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

AGGAGACCAA GTTTCAGATG                                                              20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GCGTGCAAGC ATTGATATCC                                                              20

( 2 ) INFORMATION FOR SEQ ID NO:10:

( i ) SEQUENCE CHARACTERISTICS:
        ( A ) LENGTH: 1947 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:10:

| | | | | | | |
|---|---|---|---|---|---|---|
| ATGGAGCACA | TACAGGGAGC | TTGGAAGACG | ATCAGCAATG | GCTTTGGACT | CAAAGATGCG | 60 |
| GTGTTTGATG | GCTCCAGCTG | CATCTCCCCT | ACCATTGTTC | AGCAGTTTGG | CTATCAGCGC | 120 |
| CGGGCCTCAG | ATGATGGCAA | GCTCACGGAT | TCTTCTAAGA | CAAGCAATAC | TATCCGGGTT | 180 |
| TTCTTGCCGA | ATAAGCAAAG | GACTGTGGTC | AATGTGCGGA | ATGGAATGAG | CTTACATGAC | 240 |
| TGCCTTATGA | AAGCTCTGAA | GGTGAGAGGC | CTGCAGCCAG | AGTGCTGTGC | AGTGTTCAGA | 300 |
| CTTCTCCAGG | AACACAAAGG | TAAGAAAGCA | CGCTTAGATT | GGAACACCGA | TGCCGCCTCT | 360 |
| CTGATTGGAG | AAGAACTGCA | AGTGGATTTT | TTGGATCATG | TTCCCATCAC | AACTCACAAC | 420 |
| TTTGCTCGGA | AAACGTTCCT | GAAGCTTGCA | TTCTGTGACA | TCTGTCAGAA | GTTCCTGCTA | 480 |
| AATGGATTTC | GATGTCAGAC | TTGTGGCTAC | AAGTTTCATG | AGCACTGTAG | CACCAAAGTA | 540 |
| CCTACTATGT | GTGTGGACTG | GAGTAATATC | AGACAGCTCT | TGCTGTTTCC | AAATTCCACT | 600 |
| GTTGGTGACA | GTGGAGTCCC | AGCACCACCT | TCTTTCCCAA | TGCGTCGGAT | GCGAGAATCT | 660 |
| GTTTCCCGGA | TGCCTGCTAG | TTCCCAGCAC | AGATACTCTA | CACCCCATGC | CTTCACTTTC | 720 |
| AACACCTCCA | GCCCTTCCTC | AGAAGGTTCC | CTCTCCCAGA | GGCAGAGGTC | AACGTCCACT | 780 |
| CCCAATGTCC | ACATGGTCAG | CACCACCCTG | CATGTGGACA | GCAGGATGAT | TGAGGATGCA | 840 |
| ATTCGAAGTC | ACAGTGAATC | AGCCTCACCT | TCAGCCCTGT | CCAGCAGCCC | AAACAACCTG | 900 |
| AGTCCAACAG | GCTGGTCACA | GCCCAAAACC | CCCGTGCCAG | CACAAAGAGA | GCGGGCACCA | 960 |
| GGATCTGGGA | CCCAGCAAAA | AAACAAAATT | AGGCCTCGTG | GCAGAGAGA | CTCGAGTTAT | 1020 |
| TACTGGGAAA | TAGAAGCCAG | TGAGGTGATG | CTGTCTACTC | GGATCGGGTC | AGGTTCCTTT | 1080 |
| GGCACTGTGT | ACAAGGGCAA | GTGGCATGGA | GATGTTGCAG | TAAAGATCCT | AAAGGTGGTT | 1140 |
| GACCCAACTC | CAGAGCAACT | TCAGGCCTTC | AGGAACGAGG | TGGCTGTTTT | GCGCAAAACA | 1200 |
| CGGCATGTTA | ACATCCTGCT | GTTCATGGGG | TACATGACAA | GGACAACCT | GGCGATTGTG | 1260 |
| ACTCAGTGGT | GTGAAGGCAG | CAGTCTCTAC | AAACACCTGC | ATGTCCAGGA | GACCAAATTC | 1320 |
| CAGATGTTCC | AGCTAATTGA | CATTGCCCGA | CAGACAGCTC | AGGGAATGGA | CTATTTGCAT | 1380 |
| GCAAAGAACA | TCATCCACAG | AGACATGAAA | TCCAACAATA | TATTTCTCCA | TGAAGGCCTC | 1440 |
| ACGGTGAAAA | TTGGAGATTT | TGGTTTGGCA | ACAGTGAAGT | CACGCTGGAG | TGGTTCTCAG | 1500 |
| CAGGTTGAAC | AGCCCACTGG | CTCTGTGCTG | TGGATGGCCC | CAGAAGTAAT | CCGGATGCAG | 1560 |
| GATGACAACC | CGTTCAGCTT | CCAGTCCGAC | GTGTACTCGT | ACGGCATCGT | GCTGTACGAG | 1620 |
| CTGATGGCTG | GGGAGCTTCC | CTACGCCCAC | ATCAACAACC | GAGACCAGAT | CATCTTCATG | 1680 |
| GTAGGCCGTG | GGTATGCATC | CCCTGATCTC | AGCAGGCTCT | ACAAGAACTG | CCCCAAGGCA | 1740 |
| ATGAAGAGGT | TGGTGGCTGA | CTGTGTGAAG | AAAGTCAAAG | AAGAGAGACC | TTTGTTTCCC | 1800 |
| CAGATCCTGT | CTTCCATCGA | GCTGCTTCAG | CACTCTCTGC | CGAAAATCAA | CAGGAGCGCC | 1860 |
| TCTGAGCCTT | CCCTGCATCG | GGCAGCTCAC | ACTGAGGACA | TCAATGCTTG | CACGCTGACT | 1920 |
| ACATCCCCAA | GGCTACCAGT | CTTCTAG | | | | 1947 |

( 2 ) INFORMATION FOR SEQ ID NO:11:

( i ) SEQUENCE CHARACTERISTICS:
( A ) LENGTH: 1947 base pairs
( B ) TYPE: nucleic acid
( C ) STRANDEDNESS: double
( D ) TOPOLOGY: linear ( i x ) FEATURE:
( A ) NAME/KEY: CDS
( B ) LOCATION: 1..1944

( x i ) SEQUENCE DESCRIPTION: SEQ ID NO:11:

| ATG | GAG | CAC | ATA | CAG | GGA | GCT | TGG | AAG | ACG | ATC | AGC | AAT | GGT | TTT | GGA | 48 |
| Met | Glu | His | Ile | Gln | Gly | Ala | Trp | Lys | Thr | Ile | Ser | Asn | Gly | Phe | Gly | |
| 1 | | | | 5 | | | | | 10 | | | | | 15 | | |

| TTC | AAA | GAT | GCC | GTG | TTT | GAT | GGC | TCC | AGC | TGC | ATC | TCT | CCT | ACA | ATA | 96 |
| Phe | Lys | Asp | Ala | Val | Phe | Asp | Gly | Ser | Ser | Cys | Ile | Ser | Pro | Thr | Ile | |
| | | | 20 | | | | | 25 | | | | | 30 | | | |

| GTT | CAG | CAG | TTT | GGC | TAT | CAG | CGC | CGG | GCA | TCA | GAT | GAT | GGC | AAA | CTC | 144 |
| Val | Gln | Gln | Phe | Gly | Tyr | Gln | Arg | Arg | Ala | Ser | Asp | Asp | Gly | Lys | Leu | |
| | | 35 | | | | | 40 | | | | | 45 | | | | |

| ACA | GAT | CCT | TCT | AAG | ACA | AGC | AAC | ACT | ATC | CGT | GTT | TTC | TTG | CCG | AAC | 192 |
| Thr | Asp | Pro | Ser | Lys | Thr | Ser | Asn | Thr | Ile | Arg | Val | Phe | Leu | Pro | Asn | |
| | 50 | | | | | 55 | | | | | 60 | | | | | |

| AAG | CAA | AGA | ACA | GTG | GTC | AAT | GTG | CGA | AAT | GGA | ATG | AGC | TTG | CAT | GAC | 240 |
| Lys | Gln | Arg | Thr | Val | Val | Asn | Val | Arg | Asn | Gly | Met | Ser | Leu | His | Asp | |
| 65 | | | | | 70 | | | | | 75 | | | | | 80 | |

| TGC | CTT | ATG | AAA | GCA | CTC | AAG | GTG | AGG | GGC | CTG | CAA | CCA | GAG | TGC | TGT | 288 |
| Cys | Leu | Met | Lys | Ala | Leu | Lys | Val | Arg | Gly | Leu | Gln | Pro | Glu | Cys | Cys | |
| | | | | 85 | | | | | 90 | | | | | 95 | | |

| GCA | GTG | TTC | AGA | CTT | CTC | CAC | GAA | CAC | AAA | GGT | AAA | AAA | GCA | CGC | TTA | 336 |
| Ala | Val | Phe | Arg | Leu | Leu | His | Glu | His | Lys | Gly | Lys | Lys | Ala | Arg | Leu | |
| | | | 100 | | | | | 105 | | | | | 110 | | | |

| GAT | TGG | AAT | ACT | GAT | GCT | GCG | TCT | TTG | ATT | GGA | GAA | GAA | CTT | CAA | GTA | 384 |
| Asp | Trp | Asn | Thr | Asp | Ala | Ala | Ser | Leu | Ile | Gly | Glu | Glu | Leu | Gln | Val | |
| | | 115 | | | | | 120 | | | | | 125 | | | | |

| GAT | TTC | CTG | GAT | CAT | GTT | CCC | CTC | ACA | ACA | CAC | AAC | TTT | GCT | CGG | AAG | 432 |
| Asp | Phe | Leu | Asp | His | Val | Pro | Leu | Thr | Thr | His | Asn | Phe | Ala | Arg | Lys | |
| | 130 | | | | | 135 | | | | | 140 | | | | | |

| ACG | TTC | CTG | AAG | CTT | GCC | TTC | TGT | GAC | ATC | TGT | CAG | AAA | TTC | CTG | CTC | 480 |
| Thr | Phe | Leu | Lys | Leu | Ala | Phe | Cys | Asp | Ile | Cys | Gln | Lys | Phe | Leu | Leu | |
| 145 | | | | | 150 | | | | | 155 | | | | | 160 | |

| AAT | GGA | TTT | CGA | TGT | CAG | ACT | TGT | GGC | TAC | AAA | TTT | CAT | GAG | CAC | TGT | 528 |
| Asn | Gly | Phe | Arg | Cys | Gln | Thr | Cys | Gly | Tyr | Lys | Phe | His | Glu | His | Cys | |
| | | | | 165 | | | | | 170 | | | | | 175 | | |

| AGC | ACC | AAA | GTA | CCT | ACT | ATG | TGT | GTG | GAC | TGG | AGT | AAC | ATC | AGA | CAA | 576 |
| Ser | Thr | Lys | Val | Pro | Thr | Met | Cys | Val | Asp | Trp | Ser | Asn | Ile | Arg | Gln | |
| | | | 180 | | | | | 185 | | | | | 190 | | | |

| CTC | TTA | TTG | TTT | CCA | AAT | TCC | ACT | ATT | GGT | GAT | AGT | GGA | GTC | CCA | GCA | 624 |
| Leu | Leu | Leu | Phe | Pro | Asn | Ser | Thr | Ile | Gly | Asp | Ser | Gly | Val | Pro | Ala | |
| | | 195 | | | | | 200 | | | | | 205 | | | | |

| CTA | CCT | TCT | TTG | ACT | ATG | CGT | CGT | ATG | CGA | GAG | TCT | GTT | TCC | AGG | ATG | 672 |
| Leu | Pro | Ser | Leu | Thr | Met | Arg | Arg | Met | Arg | Glu | Ser | Val | Ser | Arg | Met | |
| | 210 | | | | | 215 | | | | | 220 | | | | | |

| CCT | GTT | AGT | TCT | CAG | CAC | AGA | TAT | TCT | ACA | CCT | CAC | GCC | TTC | ACC | TTT | 720 |
| Pro | Val | Ser | Ser | Gln | His | Arg | Tyr | Ser | Thr | Pro | His | Ala | Phe | Thr | Phe | |
| 225 | | | | | 230 | | | | | 235 | | | | | 240 | |

| AAC | ACC | TCC | AGT | CCC | TCA | TCT | GAA | GGT | TCC | CTC | TCC | CAG | AGG | CAG | AGG | 768 |
| Asn | Thr | Ser | Ser | Pro | Ser | Ser | Glu | Gly | Ser | Leu | Ser | Gln | Arg | Gln | Arg | |
| | | | | 245 | | | | | 250 | | | | | 255 | | |

| TCG | ACA | TCC | ACA | CCT | AAT | GTC | CAC | ATG | GTC | AGC | ACC | ACG | CTG | CCT | GTG | 816 |
| Ser | Thr | Ser | Thr | Pro | Asn | Val | His | Met | Val | Ser | Thr | Thr | Leu | Pro | Val | |
| | | | 260 | | | | | 265 | | | | | 270 | | | |

| GAC | AGC | AGG | ATG | ATT | GAG | GAT | GCA | ATT | CGA | AGT | CAC | AGC | GAA | TCA | GCC | 864 |
| Asp | Ser | Arg | Met | Ile | Glu | Asp | Ala | Ile | Arg | Ser | His | Ser | Glu | Ser | Ala | |
| | | 275 | | | | | 280 | | | | | 285 | | | | |

| TCA | CCT | TCA | GCC | CTG | TCC | AGT | AGC | CCC | AAC | AAT | CTG | AGC | CCA | ACA | GGC | 912 |
| Ser | Pro | Ser | Ala | Leu | Ser | Ser | Ser | Pro | Asn | Asn | Leu | Ser | Pro | Thr | Gly | |
| | 290 | | | | | 295 | | | | | 300 | | | | | |

| | | | | | | | | | | | | | | | | |
|---|---|---|---|---|---|---|---|---|---|---|---|---|---|---|---|---|
| TGG | TCA | CAG | CCG | AAA | ACC | CCC | GTG | CCA | GCA | CAA | AGA | GAG | CGG | GCA | CCA | 960 |
| Trp 305 | Ser | Gln | Pro | Lys | Thr 310 | Pro | Val | Pro | Ala | Gln 315 | Arg | Glu | Arg | Ala | Pro 320 | |
| GTA | TCT | GGG | ACC | CAG | GAG | AAA | AAC | AAA | ATT | AGG | CCT | CGT | GGA | CAG | AGA | 1008 |
| Val | Ser | Gly | Thr 325 | Gln | Glu | Lys | Asn | Lys 330 | Ile | Arg | Pro | Arg | Gly 335 | Gln | Arg | |
| GAT | TCA | AGC | TAT | TAT | TGG | GAA | ATA | GAA | GCC | AGT | GAA | GTG | ATG | CTG | TCC | 1056 |
| Asp | Ser | Ser | Tyr 340 | Tyr | Trp | Glu | Ile | Glu 345 | Ala | Ser | Glu | Val | Met 350 | Leu | Ser | |
| ACT | CGG | ATT | GGG | TCA | GGC | TCT | TTT | GGA | ACT | GTT | TAT | AAG | GGT | AAA | TGG | 1104 |
| Thr | Arg | Ile 355 | Gly | Ser | Gly | Ser | Phe 360 | Gly | Thr | Val | Tyr | Lys 365 | Gly | Lys | Trp | |
| CAC | GGA | GAT | GTT | GCA | GTA | AAG | ATC | CTA | AAG | GTT | GTC | GAC | CCA | ACC | CCA | 1152 |
| His | Gly | Asp 370 | Val | Ala | Val | Lys | Ile 375 | Leu | Lys | Val | Val | Asp 380 | Pro | Thr | Pro | |
| GAG | CAA | TTC | CAG | GCC | TTC | AGG | AAT | GAG | GTG | GCT | GTT | CTG | CGC | AAA | ACA | 1200 |
| Glu 385 | Gln | Phe | Gln | Ala | Phe 390 | Arg | Asn | Glu | Val | Ala 395 | Val | Leu | Arg | Lys | Thr 400 | |
| CGG | CAT | GTG | AAC | ATT | CTG | CTT | TTC | ATG | GGG | TAC | ATG | ACA | AAG | GAC | AAC | 1248 |
| Arg | His | Val | Asn | Ile 405 | Leu | Leu | Phe | Met | Gly 410 | Tyr | Met | Thr | Lys | Asp 415 | Asn | |
| CTG | GCA | ATT | GTG | ACC | CAG | TGG | TGC | GAG | GGC | AGC | AGC | CTC | TAC | AAA | CAC | 1296 |
| Leu | Ala | Ile | Val 420 | Thr | Gln | Trp | Cys | Glu 425 | Gly | Ser | Ser | Leu | Tyr 430 | Lys | His | |
| CTG | CAT | GTC | CAG | GAG | ACC | AAG | TTT | CAG | ATG | TTC | CAG | CTA | ATT | GAC | ATT | 1344 |
| Leu | His | Val 435 | Gln | Glu | Thr | Lys | Phe 440 | Gln | Met | Phe | Gln | Leu 445 | Ile | Asp | Ile | |
| GCC | CGG | CAG | ACG | GCT | CAG | GGA | ATG | GAC | TAT | TTG | CAT | GCA | AAG | AAC | ATC | 1392 |
| Ala | Arg 450 | Gln | Thr | Ala | Gln | Gly 455 | Met | Asp | Tyr | Leu | His 460 | Ala | Lys | Asn | Ile | |
| ATC | CAT | AGA | GAC | ATG | AAA | TCC | AAC | AAT | ATA | TTT | CTC | CAT | GAA | GGC | TTA | 1440 |
| Ile 465 | His | Arg | Asp | Met | Lys 470 | Ser | Asn | Asn | Ile | Phe 475 | Leu | His | Glu | Gly | Leu 480 | |
| ACA | GTG | AAA | ATT | GGA | GAT | TTT | GGT | TTG | GCA | ACA | GTA | AAG | TCA | CGC | TGG | 1488 |
| Thr | Val | Lys | Ile | Gly 485 | Asp | Phe | Gly | Leu | Ala 490 | Thr | Val | Lys | Ser | Arg 495 | Trp | |
| AGT | GGT | TCT | CAG | CAG | GTT | GAA | CAA | CCT | ACT | GGC | TCT | GTC | CTC | TGG | ATG | 1536 |
| Ser | Gly | Ser | Gln 500 | Gln | Val | Glu | Gln | Pro 505 | Thr | Gly | Ser | Val | Leu 510 | Trp | Met | |
| GCC | CCA | GAG | GTG | ATC | CGA | ATG | CAG | GAT | AAC | AAC | CCA | TTC | AGT | TTC | CAG | 1584 |
| Ala | Pro | Glu 515 | Val | Ile | Arg | Met | Gln 520 | Asp | Asn | Asn | Pro | Phe 525 | Ser | Phe | Gln | |
| TCG | GAT | GTC | TAC | TCC | TAT | GGC | ATC | GTA | TTG | TAT | GAA | CTG | ATG | ACG | GGG | 1632 |
| Ser | Asp 530 | Val | Tyr | Ser | Tyr | Gly 535 | Ile | Val | Leu | Tyr | Glu 540 | Leu | Met | Thr | Gly | |
| GAG | CTT | CCT | TAT | TCT | CAC | ATC | AAC | AAC | CGA | GAT | CAG | ATC | ATC | TTC | ATG | 1680 |
| Glu 545 | Leu | Pro | Tyr | Ser | His 550 | Ile | Asn | Asn | Arg | Asp 555 | Gln | Ile | Ile | Phe | Met 560 | |
| GTG | GGC | CGA | GGA | TAT | GCC | TCC | CCA | GAT | CTT | AGT | AAG | CTA | TAT | AAG | AAC | 1728 |
| Val | Gly | Arg | Gly | Tyr 565 | Ala | Ser | Pro | Asp | Leu 570 | Ser | Lys | Leu | Tyr | Lys 575 | Asn | |
| TGC | CCC | AAA | GCA | ATG | AAG | AGG | CTG | GTA | GCT | GAC | TGT | GTG | AAG | AAA | GTA | 1776 |
| Cys | Pro | Lys | Ala 580 | Met | Lys | Arg | Leu | Val 585 | Ala | Asp | Cys | Val | Lys 590 | Lys | Val | |
| AAG | GAA | GAG | AGG | CCT | CTT | TTT | CCC | CAG | ATC | CTG | TCT | TCC | ATT | GAG | CTG | 1824 |
| Lys | Glu | Glu | Arg 595 | Pro | Leu | Phe | Pro | Gln 600 | Ile | Leu | Ser | Ser | Ile 605 | Glu | Leu | |
| CTC | CAA | CAC | TCT | CTA | CCG | AAG | ATC | AAC | CGG | AGC | GCT | TCC | GAG | CCA | TCC | 1872 |
| Leu | Gln | His | Ser 610 | Leu | Pro | Lys | Ile | Asn 615 | Arg | Ser | Ala | Ser | Glu 620 | Pro | Ser | |

```
TTG  CAT  CGG  GCA  GCC  CAC  ACT  GAG  GAT  ATC  AAT  GCT  TGC  ACG  CTG  ACC       1920
Leu  His  Arg  Ala  Ala  His  Thr  Glu  Asp  Ile  Asn  Ala  Cys  Thr  Leu  Thr
625                      630                 635                      640

ACG  TCC  CCG  AGG  CTG  CCT  GTC  TTC  TAG                                          1947
Thr  Ser  Pro  Arg  Leu  Pro  Val  Phe
                    645
```

( 2 ) INFORMATION FOR SEQ ID NO:12:

( i ) SEQUENCE CHARACTERISTICS:
    ( A ) LENGTH: 648 amino acids
    ( B ) TYPE: amino acid
    ( D ) TOPOLOGY: linear ( i i ) MOLECULE TYPE: protein ( x i ) SEQUENCE DESCRIPTION: SEQ ID NO:12:

```
Met  Glu  His  Ile  Gln  Gly  Ala  Trp  Lys  Thr  Ile  Ser  Asn  Gly  Phe  Gly
 1                  5                   10                      15

Phe  Lys  Asp  Ala  Val  Phe  Asp  Gly  Ser  Ser  Cys  Ile  Ser  Pro  Thr  Ile
               20                  25                      30

Val  Gln  Gln  Phe  Gly  Tyr  Gln  Arg  Arg  Ala  Ser  Asp  Asp  Gly  Lys  Leu
          35                  40                       45

Thr  Asp  Pro  Ser  Lys  Thr  Ser  Asn  Thr  Ile  Arg  Val  Phe  Leu  Pro  Asn
     50                       55                       60

Lys  Gln  Arg  Thr  Val  Val  Asn  Val  Arg  Asn  Gly  Met  Ser  Leu  His  Asp
65                       70                       75                        80

Cys  Leu  Met  Lys  Ala  Leu  Lys  Val  Arg  Gly  Leu  Gln  Pro  Glu  Cys  Cys
                    85                       90                       95

Ala  Val  Phe  Arg  Leu  Leu  His  Glu  His  Lys  Gly  Lys  Lys  Ala  Arg  Leu
               100                 105                     110

Asp  Trp  Asn  Thr  Asp  Ala  Ala  Ser  Leu  Ile  Gly  Glu  Glu  Leu  Gln  Val
               115                 120                     125

Asp  Phe  Leu  Asp  His  Val  Pro  Leu  Thr  Thr  His  Asn  Phe  Ala  Arg  Lys
     130                 135                     140

Thr  Phe  Leu  Lys  Leu  Ala  Phe  Cys  Asp  Ile  Cys  Gln  Lys  Phe  Leu  Leu
145                      150                     155                      160

Asn  Gly  Phe  Arg  Cys  Gln  Thr  Cys  Gly  Tyr  Lys  Phe  His  Glu  His  Cys
                    165                 170                     175

Ser  Thr  Lys  Val  Pro  Thr  Met  Cys  Val  Asp  Trp  Ser  Asn  Ile  Arg  Gln
               180                 185                     190

Leu  Leu  Leu  Phe  Pro  Asn  Ser  Thr  Ile  Gly  Asp  Ser  Gly  Val  Pro  Ala
          195                 200                     205

Leu  Pro  Ser  Leu  Thr  Met  Arg  Arg  Met  Arg  Glu  Ser  Val  Ser  Arg  Met
     210                 215                     220

Pro  Val  Ser  Ser  Gln  His  Arg  Tyr  Ser  Thr  Pro  His  Ala  Phe  Thr  Phe
225                      230                     235                      240

Asn  Thr  Ser  Ser  Pro  Ser  Ser  Glu  Gly  Ser  Leu  Ser  Gln  Arg  Gln  Arg
               245                 250                     255

Ser  Thr  Ser  Thr  Pro  Asn  Val  His  Met  Val  Ser  Thr  Thr  Leu  Pro  Val
               260                 265                     270

Asp  Ser  Arg  Met  Ile  Glu  Asp  Ala  Ile  Arg  Ser  His  Ser  Glu  Ser  Ala
     275                 280                     285

Ser  Pro  Ser  Ala  Leu  Ser  Ser  Pro  Asn  Asn  Leu  Ser  Pro  Thr  Gly
     290                 295                     300

Trp  Ser  Gln  Pro  Lys  Thr  Pro  Val  Pro  Ala  Gln  Arg  Glu  Arg  Ala  Pro
305                 310                     315                      320
```

-continued

| | | | | | | | | | | | | | | | |
|---|---|---|---|---|---|---|---|---|---|---|---|---|---|---|---|
| Val | Ser | Gly | Thr | Gln | Glu | Lys | Asn | Lys | Ile | Arg | Pro | Arg | Gly | Gln | Arg |
| | | | | 325 | | | | | 330 | | | | | 335 | |
| Asp | Ser | Ser | Tyr | Tyr | Trp | Glu | Ile | Glu | Ala | Ser | Glu | Val | Met | Leu | Ser |
| | | | 340 | | | | 345 | | | | | 350 | | | |
| Thr | Arg | Ile | Gly | Ser | Gly | Ser | Phe | Gly | Thr | Val | Tyr | Lys | Gly | Lys | Trp |
| | | 355 | | | | | 360 | | | | | 365 | | | |
| His | Gly | Asp | Val | Ala | Val | Lys | Ile | Leu | Lys | Val | Val | Asp | Pro | Thr | Pro |
| | 370 | | | | | 375 | | | | | 380 | | | | |
| Glu | Gln | Phe | Gln | Ala | Phe | Arg | Asn | Glu | Val | Ala | Val | Leu | Arg | Lys | Thr |
| 385 | | | | | 390 | | | | | 395 | | | | | 400 |
| Arg | His | Val | Asn | Ile | Leu | Leu | Phe | Met | Gly | Tyr | Met | Thr | Lys | Asp | Asn |
| | | | | 405 | | | | | 410 | | | | | 415 | |
| Leu | Ala | Ile | Val | Thr | Gln | Trp | Cys | Glu | Gly | Ser | Ser | Leu | Tyr | Lys | His |
| | | | 420 | | | | | 425 | | | | | 430 | | |
| Leu | His | Val | Gln | Glu | Thr | Lys | Phe | Gln | Met | Phe | Gln | Leu | Ile | Asp | Ile |
| | | 435 | | | | | 440 | | | | | 445 | | | |
| Ala | Arg | Gln | Thr | Ala | Gln | Gly | Met | Asp | Tyr | Leu | His | Ala | Lys | Asn | Ile |
| | 450 | | | | | 455 | | | | | 460 | | | | |
| Ile | His | Arg | Asp | Met | Lys | Ser | Asn | Asn | Ile | Phe | Leu | His | Glu | Gly | Leu |
| 465 | | | | | 470 | | | | | 475 | | | | | 480 |
| Thr | Val | Lys | Ile | Gly | Asp | Phe | Gly | Leu | Ala | Thr | Val | Lys | Ser | Arg | Trp |
| | | | | 485 | | | | | 490 | | | | | 495 | |
| Ser | Gly | Ser | Gln | Gln | Val | Glu | Gln | Pro | Thr | Gly | Ser | Val | Leu | Trp | Met |
| | | | 500 | | | | | 505 | | | | | 510 | | |
| Ala | Pro | Glu | Val | Ile | Arg | Met | Gln | Asp | Asn | Asn | Pro | Phe | Ser | Phe | Gln |
| | | 515 | | | | | 520 | | | | | 525 | | | |
| Ser | Asp | Val | Tyr | Ser | Tyr | Gly | Ile | Val | Leu | Tyr | Glu | Leu | Met | Thr | Gly |
| | 530 | | | | | 535 | | | | | 540 | | | | |
| Glu | Leu | Pro | Tyr | Ser | His | Ile | Asn | Asn | Arg | Asp | Gln | Ile | Ile | Phe | Met |
| 545 | | | | | 550 | | | | | 555 | | | | | 560 |
| Val | Gly | Arg | Gly | Tyr | Ala | Ser | Pro | Asp | Leu | Ser | Lys | Leu | Tyr | Lys | Asn |
| | | | | 565 | | | | | 570 | | | | | 575 | |
| Cys | Pro | Lys | Ala | Met | Lys | Arg | Leu | Val | Ala | Asp | Cys | Val | Lys | Lys | Val |
| | | | 580 | | | | | 585 | | | | | 590 | | |
| Lys | Glu | Glu | Arg | Pro | Leu | Phe | Pro | Gln | Ile | Leu | Ser | Ser | Ile | Glu | Leu |
| | | 595 | | | | | 600 | | | | | 605 | | | |
| Leu | Gln | His | Ser | Leu | Pro | Lys | Ile | Asn | Arg | Ser | Ala | Ser | Glu | Pro | Ser |
| | 610 | | | | | 615 | | | | | 620 | | | | |
| Leu | His | Arg | Ala | Ala | His | Thr | Glu | Asp | Ile | Asn | Ala | Cys | Thr | Leu | Thr |
| 625 | | | | | 630 | | | | | 635 | | | | | 640 |
| Thr | Ser | Pro | Arg | Leu | Pro | Val | Phe | | | | | | | | |
| | | | | 645 | | | | | | | | | | | |

DETECTION METHOD FOR C-RAF-1 GENES

This application is a divisional of application Ser. No. 08/185,282, filed Jan. 24, 1994, now U.S. Pat. No. 5,618,670, which is a continuation of Ser. No. 07/759,238 filed Sep. 16, 1991, now abandoned, which is a continuation-in-part of Ser. No. 07/236,947 filed Aug. 26, 1988 which is now U.S. Pat. No. 5,156,841.

BACKGROUND OF THE INVENTION

1. Field of the Invention

The present invention relates to (1) a method of identifying an individual at an increased risk for developing cancer, (2) a method for determining a prognosis of patients afflicted with cancer, and (3) a method for determining the proper course of treatment for a patient afflicted with cancer.

2. Background Information

Lung cancer claims more lives in the United States than any other neoplasm (R. S. Finley, *Am. Pharm.* NS29, 39 (1989)), and of the various forms lung adenocarcinomas have one of the worst prognoses (T. P. Miller, *Semin. Oncol.* 17, 11 (1990)). The incidence of adenocarcinoma of the lung (ACL) in the United States is also quickly rising (I. Linnoila, Hematol. *Oncol. North. Am.* 4, 1027 (1990); J. B. Sorensen, H. H. Hansen, *Cancer Surviv.* 8, 671 (1989)). In order to gain insight into this complex and deadly disease, a model system for its study has been developed. For such a model to provide clinically relevant data several criteria must be met. The tumors produced should be histologically equivalent to their human counterparts, tumor induction must be reliable and reproducible, and the numbers generated must be great enough to provide statistical significance. To satisfy these conditions a system has been created which uses two inbred souse strains (NFS/n and AKR) along with transplacental exposure to the potent carcinogen N-ethyl-N-nitrosourea (ENU) and promotion with the antioxidant butylated hydroxytoluene (BHT). The resulting tumors were examined for, altered expression or structural mutations of genes implicated in lung tumor development such as ras, mvc, and raf oncogenes (C. D. Little et al., *Nature* 306, 194 (1983); P. E. Kiefer et al., *Cancer Res.,* 47, 6236 (1987); E. Santos et al., *Science* 223, 661 (1984); S. Rodenhuis, *N. Engl. J. Med.* 317, 929 (1987); M. Barbacid, *Eur. J. Clin. Invest,* 20, 225 (1990); U. R. Rapp et al., *J. Int. Assoc. for the Study of Lung Cancer* 4, 162 (1988); M. J. Birrer et al., *Ann. Rev. Med.* 40, 305 (1989); G. Sithanandam et al., *Oncogene* 4, 451 (1989)).

raf proto-oncogenes are evolutionarily highly conserved genes encoding cytoplasmic serine/threonine specific kinases, which function in mitogen signal transduction (reviewed in U. R. Rapp et al., *The Oncogene Handbook,* T. Curran et al., Eds. (Elsevier Science Publishers, The Netherlands, 1988), pp. 115–154; U. R. Rapp, *Oncogene* 6, 495 (1991)). The three known active members in the raf family encode phosphoproteins of similar size (72/74 kD for Raf-1; 68 kD for A-Raf-1, and 74 kD for B-Raf (U. R. Rapp et al., in *Retroviruses and Human Pathology,* R. Gallo et al., Eds. (Humana Press, Clifton, N.J. 1985), pp. 449–472; T. W. Beck et al., *Nucleic Acids Res,* 15, 595 (1987); G. Sithanandam et al., *Oncogene* 5, 1775 (1990))). Raf-1 was first identified as the cellular homologue of v-raf (H. W. Jansen et al., *Nature* 307, 218 (1984)), the transforming gene of 3611 MSV (U. R. Rapp et al., *J. Virol.* 45, 914 (1983); U. R. Rapp et al., *Proc. Natl. Acad. Sci. USA* 80, 4218 (1983)). Amino acid comparisons of raf family genes shows three conserved regions [CR1, CR2, CR3] (T. W. Beck et al., *Nucleic Acids Res,* 15, 595 (1987)); CR1 is a regulatory region surrounding a Cys finger consensus sequence, CR2 is a serine/threonine rich region, and CR3 represents the kinase domain. Raf-1 has been mapped to chromosome 3p25 in humans (S. J. O'Brien et al., *Science* 223, 71 (1984)), and this region has been found to be frequently altered in small cell lung carcinoma (SCLC) (J. Whang-Peng et al., *Cancer Genet. Cytogenet.* 6, 119 (1982); J. M. Ibson et al., *J. Cell. Biochem.* 33, 267 (1987)), familial renal cell carcinoma (A. J. Cohen et al., *N. Engl. J. Med.* 301, 592 (1979); G. Kovacs et al., *Int. J. Cancer* 40, 171 (1987)), mixed parotid gland tumors (J. Mark et al., *Hereditas* 96, 141 (1982)), and ovarian cancer (K. Tanaka et al., *Cancer Genet. Cytogenet.* 43, 1 (1989)).

Raf genes are differentially expressed in various tissues (S. M. Storm et al., *Oncogene* 5, 345 (1990)). c-raf-1 has been found to be expressed ubiquitously, though absolute levels vary between tissues. A-raf-1 is present predominantly in the urogenital tissues, whereas B-Raf is most abundant in cerebrum and testis. The ubiquitous c-Raf-1 kinase is regulated by tyrosine and serine phosphorylations that result from activated growth factor receptor kinases (D. K. Morrison et al., *Cell* 58, 648 (1989); D. K. Morrison et al., *Proc. Natl. Acad. Sci. USA* 85, 8855 (1989); K. S. Kovacina et al., *J. Biol. Chem.* 265, 12115 (1990); P. J. Blackshear et al., *J. Biol. Chem.* 265, 12131 (1990); M. P. Carroll et al., *J. Biol. Chem.* 265, 19812 (1990); J. N. Siegel et al., *J. Biol. Chem.* 265, 18472 (1990); B. C. Turner et al., *Proc. Natl. Acad. Sci. USA* 88, 1227 (1991); M. Baccarini et al., *EMBO J.* 9, 3649 (1990); H. App et al., *Mol. Cell. Biol.* 11, 913 (1991)). Raf-1 operates downstream of Ras in mitogen signal transduction as judged by experiments using antibody microinjection (M. R. Smith et al., *Nature* 320, 540 (1986)), c-raf-1 antisense expression constructs (W. Kolch et al., *Nature* 349, 426 (1991)), dominant negative mutants (W. Kolch et al., *Nature* 349, 426 (1991)), and Raf revertant cells. Studies with NIH3T3 cells and brain tissue demonstrated that mitogen treatment induces Raf-1 kinase activity and causes a transitory relocation of the active enzyme from the cytoplasm to the nucleus and perinuclear area (Z. Olah et al., *Exp. Brain. Res.* (in press); U. R. Rapp et al., in *Cold Spring Harbor Symposia on Quantitative Biology,* Vol. LIII, Eds. (Cold Spring Harbor Laboratory Press, Cold Spring Harbor, N.Y. 1988) pp. 173–184).

Raf-1 coupling has been examined in more than a dozen receptor systems and all strong mitogens stimulated Raf-1 kinase activity (U. R. Rapp, *Oncogene* 6, 495 (1991); D. K. Morrison et al., *Cell* 58, 648 (1989); D. K. Morrison et al., *Proc. Natl. Acad. Sci. USA* 85, 8855 (1989); K. S. Kovacina et al., *J. Biol. Chem.* 265, 12115 (1990); P. J. Blackshear et al., *J. Biol. Chem.* 265, 12131 (1990); M. P. Carroll et al., *J. Biol. Chem.* 265, 19812 (1990); J. N. Siegel et al., *J. Biol. Chem.* 265, 18472 (1990); B. C. Turner et al., *Proc. Natl. Acad. Sci. USA* 88, 1227 (1991); M. Baccarini et al., *EMBO J.* 9, 3649 (1990); H. App et al., *Mol. Cell. Biol,* 11, 913 (1991)), and this stimulation correlated with an increase in Raf-1 phosphorylation leading to a shift in apparent molecular weight.

SUMMARY OF THE INVENTION

It is an object of this invention to provide a method of identifying an individual at an increased risk for developing cancer.

It is another object of this invention to provide a method for determining a prognosis in patients afflicted with cancer.

It is a further object of this invention to provide a method for determining the proper course of treatment for a patient afflicted with cancer.

Further objects and advantages of the present invention will be clear from the description that follows.

In one embodiment, the present invention relates to a method of identifying an individual at an increased risk for developing cancer, comprising:

amplifying a region of the c-raf-1 gene;

analyzing products of the amplification for evidence of mutation; and classifying an individual having one or more mutations in the region as having an increased risk for developing cancer.

In another embodiment, the present invention relates to a method for determining a prognosis in patients afflicted with cancer, comprising:

amplifying a region of the c-raf-1 gene;

analyzing products of the amplification for evidence of mutation; and classifying patients having no mutation in said region as being less likely to suffer disease relapse or having an increased chance of survival than those patients having one or more mutations in said region.

In a further embodiment, the present invention relates to a method for determining the proper course of treatment for a patient afflicted with cancer, comprising:

amplifying a region of the c-raf-1 gene;

analyzing products of said amplification for evidence of mutation;

identifying a patient having at least one mutation in said region, which patient may require treatment proper for patients having a lesser chance of survival or decreased time to relapse; and identifying a patient lacking mutations in said region, which patients may require treatment proper for patients having a greater chance of survival or being less likely to suffer disease relapse.

DETAILED DESCRIPTION OF THE INVENTION

The present invention relates to methods that involve amplifying a region of the c-raf-1 gene (the sequence of a mouse c-raf-1 gene is shown in SEQ ID NO:10; the nucleotide and corresponding amino acid sequence of a human c-raf-1 gene is shown in SEQ ID NO:11 and SEQ ID NO:12, respectively).

Figure 6:
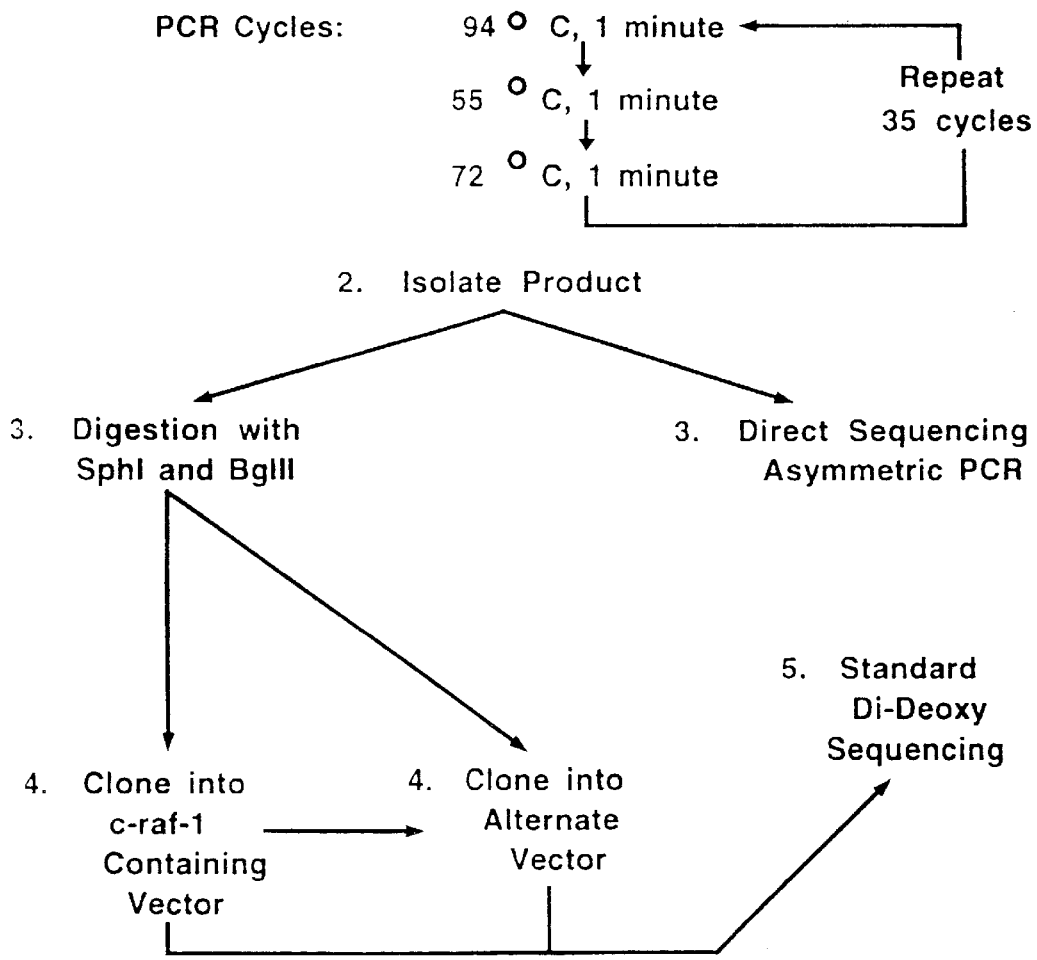
FIG. 6. Schematic for Identifying c-raf-1 mutations. Primers 1 and 2 are shown in SEQ ID NO:8 and SEQ ID NO:9, respectively.

In one embodiment, the present invention relates to a method of identifying an individual at an increased risk for developing cancer (preferably, lung cancer, T-cell lymphomas, renal cell carcinoma, ovarian carcinoma, and mixed parotid gland tumors) comprising: amplifying a region (preferably by using the polymerase chain reaction method(PCR) or by cloning techniques) of the c-raf-1 gene of the individual (SEQ ID NO:11)(in one preferred embodiment, the region encodes amino acids 514 to 535 of SEQ ID NO:12); analyzing products of the amplification for evidence of mutation (preferably by DNA sequencing of the region) and classifying an individual having one or more mutations in the region as having an increased risk for developing cancer. In one prefered embodiment, the region encodes amino acids 500 to 550 of SEQ ID NO:12 or amino acids 450 to 630 of SEQ ID NO:12. In another prefered embodiment, the PCR method employs a primer comprising the sequence shown in SEQ ID NO:9 and a primer comprising the sequence shown in SEQ ID NO:8. In another prefered embodiment, the method comprises the steps shown in FIG. 6.

In another embodiment, the present invention relates to a method for determining a prognosis in a patient afflicted with cancer (preferably, those cancers listed above). The method comprises: amplifying the region of the c-raf-1 gene as described above; analyzing products of the amplification for evidence of mutation as described above; and classifying a patient having no mutation in the region as being less likely to suffer disease relapse or having an increased chance of survival than a patient having one or more mutations in the region.

In another embodiment, the present invention relates to a method for determining the proper course of treatment for a patient afflicted with cancer (preferably, those cancers listed above), comprising: amplifying a region (described above) of the c-raf-1 gene as described above; analyzing products of the amplification for evidence of mutation as described above; identifying a patient having at least one mutation in the region, which patient may require treatment proper for patients having a lesser chance of survival or decreased time to relapse; and identifying a patient lacking mutations in the region, which patients may require treatment proper for patients having a greater chance of survival or being less likely to suffer disease relapse.

Administration of therapeutic agents (cytotoxic or cytostatic) tailored to recognize the mutant Raf-1 protein but not normal Raf-1 could specifically target tumor cells for death of growth inhibition. Such agents could be comprised of cytotoxic T-cells, antibodies, and/or specifically designed chemical compounds.

The following Examples demonstrate consistent point mutations of the c-raf-1 proto-oncogene, within a small region of the kinase domain, in a mouse model for chemical tumor induction. This is the first demonstration of point mutated raf genes in vivo, and the first isolation of activating in vivo point mutations in the kinase domain of a proto-oncogene. The tumors examined show a selective specificity for Raf-1 mutations as another family of genes, the ras proto-oncogenes which are frequently activated by point mutation in both animal and human tumors (S. Rodenhuis et al., *Am. Rev. Respir. Dis.* 142, S27–30; T. R. Devereux et al., *Carcinogenesis* 12, 299 (1991)), is not involved.

The present invention is described in further detail in the following non-limiting examples.

EXAMPLES

The following protocols and experimental details are referenced in the examples that follow:

RNA Isolation. Tumors were excised, a small portion minced in PBS (phosphate buffered saline solution) for passaging in nude nice, frozen immediately in a dry ice/ethanol bath, and stored at −70° until RNA extraction. Frozen tissues were minced on wet ice in a guanidine thiocyanate buffer (4M guanidine thiocyanate 10 mM EDTA, 2% N-lauryl sarcosine, 2% beta-mercaptoethanol, 10 mM Tris (pH=7.6)), disrupted in a Dounce homogenizer, and extracted three times with phenol: chloroform: isoamyl alcohol (24:24:2). Supernatants were then transferred to SW41 tubes, 100 μg of cesium chloride per ml was added to the supernatant which was then underlayed with one half saturated cesium chloride in 10 mM EDTA (pH=7.0; index of refraction 1.3995–1.4000), and centrifuged at 25,000 rpm for 20 hours in a Sorvall SW-41TI rotor using a Beckman model L5-50 ultracentrifuge. Supernatants were removed and RNA pellets dissolved in 4 ml resuspension buffer (10 mM Tris-HCl pH=7.6, 5% beta-mercaptoethanol, 0.5% N-lauryl sarcosine, 10 mM EDTA), extracted once with phenol:chloroform:isoamyl alcohol, sodium acetate added to 0.12M and RNA precipatated with two volumes ethanol at −20° C. overnight. Precipitates were centrifuged at 9,000 rpm in a Sorvall SS-34 rotor for 30 minutes, and pellets redissolved in RNA sample buffer (10 mM Tris pH=7.4, 1 mM EDTA, 0.05% sodium dodecyl sulfate) and concentrations determined by absorbance at 260 nm. Poly (A)$^+$ RNA was isolated by binding to oligo dT cellulose columns in high salt (10 mM Tris pH=7.4, 1 mM EDTA, 0.05% SDS, 500 mM NaCl), and eluting with RNA sample buffer heated to 40° C.

Northern Blotting. 5 μg poly(A)$^+$ RNA per lane was ethanol precipitated, desiccated, resuspended in loading buffer (20 mM MOPS pH=6.8, 5 mM sodium acetate, 1 mM EDTA, 50% formamide, 6% formaldehyde), heated at 65° C. for 5 min., quick chilled on wet ice for 10 min., and electrophoresed through a 0.7% agarose gel containing 2.2M formaldehyde, 20 mM MOPS [pH=6.8], 5 mM sodium acetate, and 1 mM EDTA. Gels were then blotted overnight onto nitrocellulose filters via capillary transfer in 20X SSC, filters were washed in 3X SSC for 10 min. and baked at 80° C. for 2 hours.

Hybridizations. Filters were prehybridized at 42° C. in 5X SSC, 50% formamide, 20 mM sodium phosphate pH=6.8, 200 μg/ml PVP-40, 200 μg/ml ficoll 400, 200 μg/ml bovine serum albumin, and 200 μg/ml sonicated sheared salmon sperm DNA. Blots were then hybridized with 500,000 cpm/ml of random primed $^{32}$P labeled probes overnight at 42° C. in prehybridization solution with 5% dextran sulfate. Blots were washed with agitation in 2X SSC, 0.1% SDS at room temperature six times for 20 minutes each wash, then washed once at 45° C. in 0.1X SSC for 15 minutes. Filters were exposed to X-AR 5 film at −70° C.

Example 1

Tumor Induction

Figure 1:
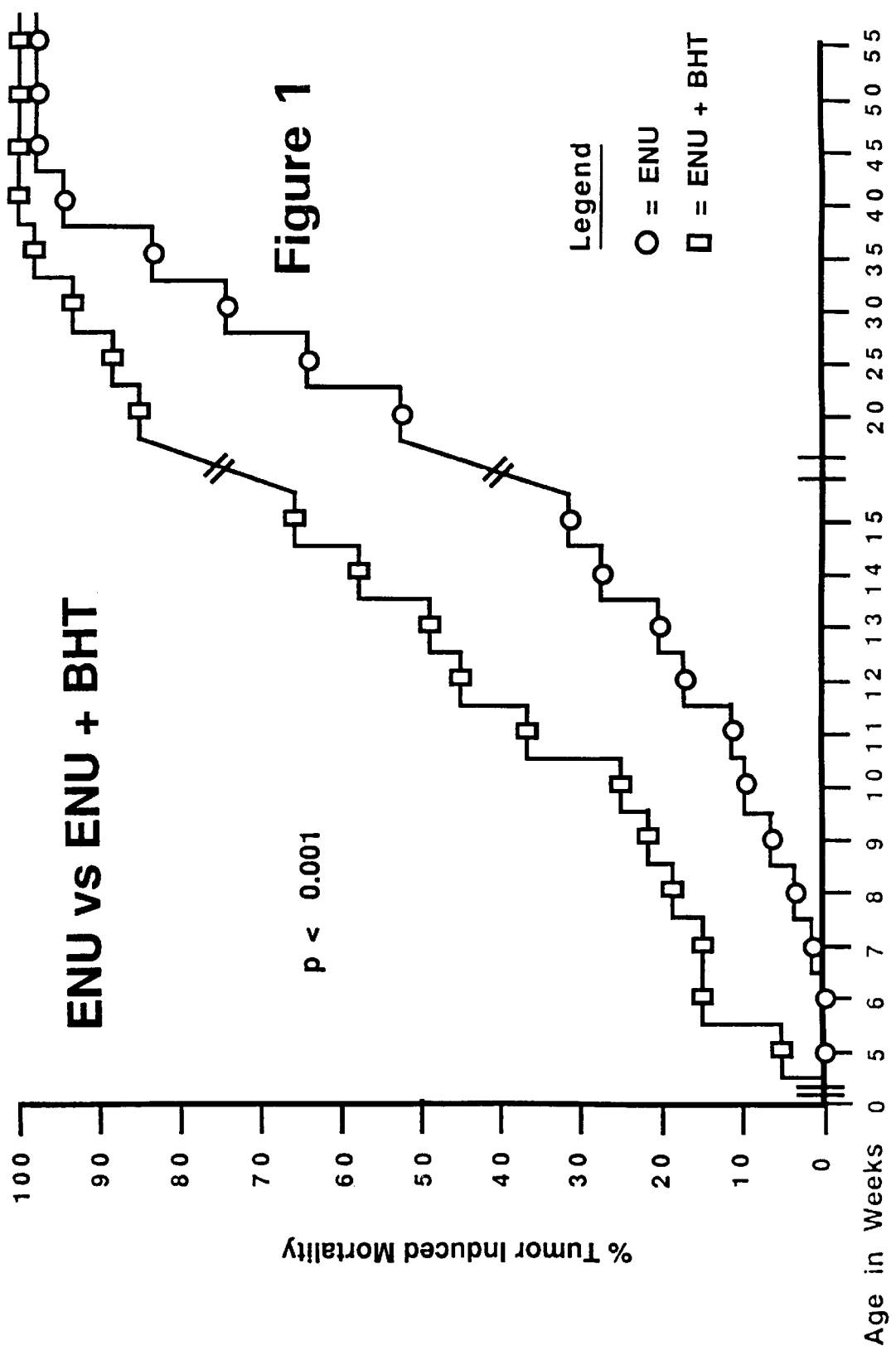
FIG. 1. Effect of BHT promotion on ENU tumorigenesis in NFS/n x AKR mice. The X-axis represents percent tumor induced mortality within each group, and the Y-axis reflects age in weeks. All animals were exposed to ENU transplacentally at a dose of 0.5 mM/Kg of mother's body weight on day 16 of gestation (presence of vaginal plug was scored as day one). At two weeks of age mice were weaned into two separate groups and separated by sex. Both groups were housed in identical cages and supplied with food (Purina Lab Chow) and water ad libitum. Beginning at three weeks of age, group 2A (O) was given weekly intraperitoneal (i.p.) injection of corn oil (0.1 ml), and group 2B (◇) received weekly i.p. injections of BHT (20 mg/Kg of body weight) dissolved in corn oil. Administration of BHT reduces the mean age of mortality from approximately 20 weeks to 13, and decreases the initial age of mortality. These curves are significantly different ($p \leq 0.001$) as judged by a 2-tailed Cox test. In both groups the rate of tumorigenesis was identical for males and females.

NFS female mice were mated with AKR males and pregnant females given a transplacental injection of 1-ethyl-1-nitrosourea (ENU) at a dosage of 0.5 mM/Kg mother's body weight on day 16 of gestation, counting plug date as day one. ENU was chosen for tumor induction since it is a very potent direct acting carcinogen capable of modifying any base in vivo (Singer, B. et al., 1983. *Molecular Biology of Mutagens and Carcinogens*, Plenum Press, New York). ENU alkylates all tissues with roughly the same efficiency (E. Scherer et al., *Cancer Lett.* 46, 21 (1989)) and has a very short half life in vivo (E. M. Faustman et al., *Teratology* 40, 199 (1989)) allowing specific mutagenesis of tissues which are mitotically active at a particular time. NFS and AKR were chosen as parental strains based on earlier studies which showed then to be particularly susceptible to lung tumors following ENU exposure (B. A. Diwan et al., *Cancer Res.* 34, 764 (1974); S. L. Kauffman, *JNCI* 57, 821 (1976)). With this procedure nearly 100% of the offspring develop lung adenocarcinomas and approximately 70% develop, in addition, T-cell lymphomas with a mean latency of approximately 20 weeks. In order to achieve more rapid tumor development, weaning mice were treated with weekly injections of a tumor promoter, the antioxidant butylated hydroxytoluene or BHT (20 mg/kg body weight dissolved in corn oil). BHT was used as it has been demonstrated to cause lung lesions and hyperplasia when injected into mice (A. A. Marino et al., *Proc. Soc. Exp. Biol. Med.* 140, 122 (1972); H. Witschi et al., *Proc. Soc. Exp. Biol. Med.*, 147, 690 (1974); N. Ito et al., *CRC Crit. Rev. Toxicol.* 15, 109 (1984)). In the present system it nearly doubles the rate at which tumors develop. FIG. 1 compares tumor induced mortality with age of animals for those receiving ENU alone, and those receiving ENU and promoted with BHT. These curves demonstrate that when BHT is given the mean age of tumor induced mortality decreases from approximately 20 weeks to around 12, and there is also a decrease in initial latency. These curves are significantly different with a confidence limit greater than 99.99% using a 2-tailed Cox test. In addition, BHT promotion, while increasing the rate at which tumors develop, does not affect the tumor spectrum.

Example 2

Oncogene Expression

Figure 2:
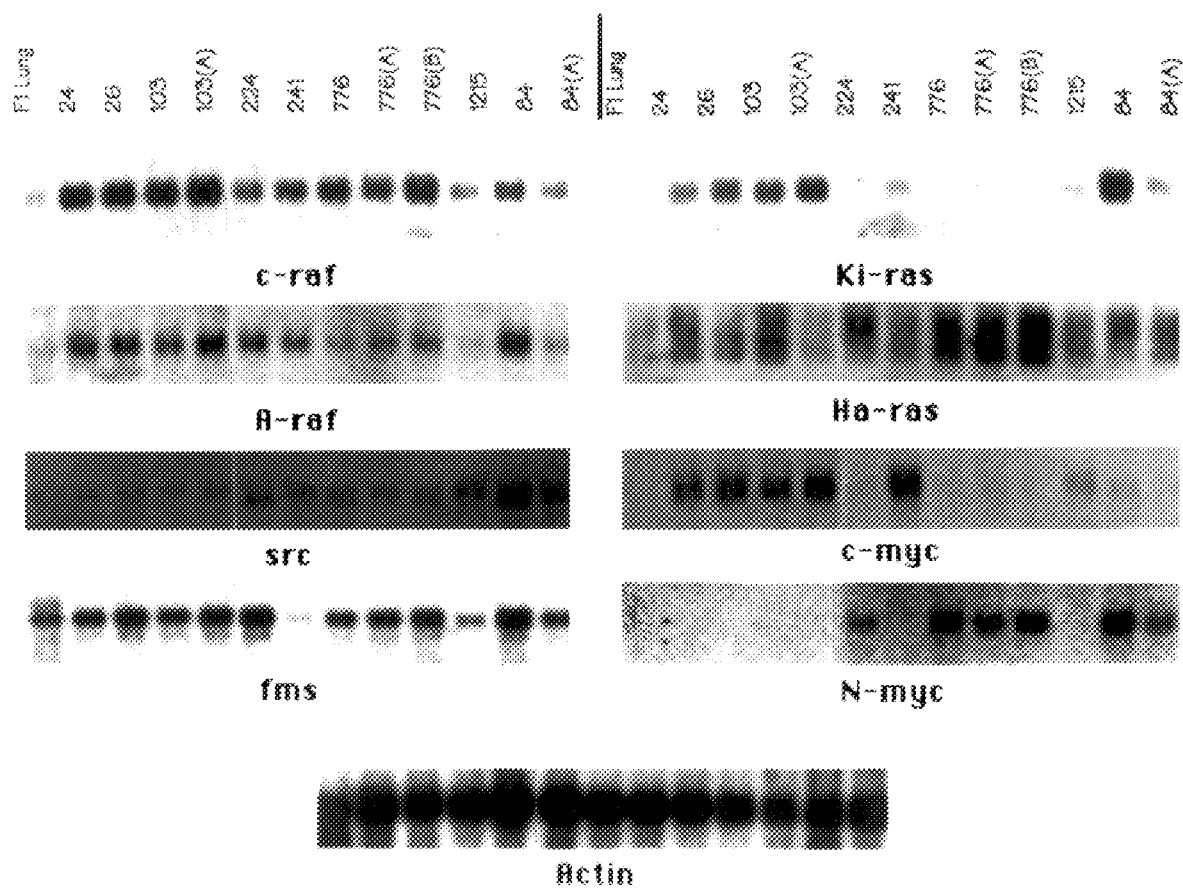
FIG. 2. Northern blot analysis of proto-oncogene expression levels in ENU induced tumors.
Figure 3A:
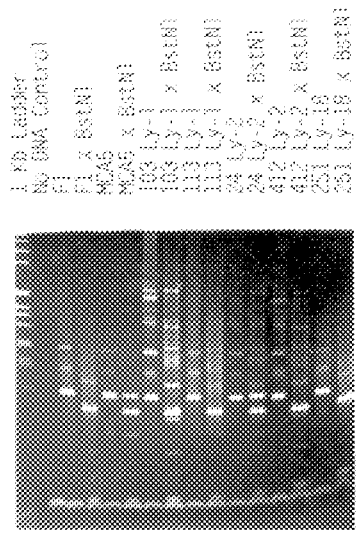
FIG. 3. Diagnostic digestion of PCR amplified Ki-ras genes from ENU induced tumors. Genomic DNA was isolated from a cesium chloride gradient during RNA preparations. In each case 10 ng was amplified via PCR (95° C., 5 min. followed by 35 cycles of 95° C., 1 min.→55° C., 1 min.→72°, 1 min.) with 2 units of Taq I polymerase. The primers used (K1; 5'-AACTTGTGGTGGTTGGACCT-3'→ (SEQ ID NO:6) and K2; ←3'-GTCTTAGT-GAAACACCTACT-5' (SEQ ID NO:7)) generate a 79 b.p. product. The primer K1 ends at codon 12 and contains a mismatch from normal mouse (Ki-ras sequence its 18th nucleotide (G→C) creating a BstNI site (CCTGG) in conjunction with a normal codon 12 (GGT). Digestion of amplified product from a normal allele with BstNI produces two products of 19 and 60 b.p., whereas a mutation in one of the first two positions of codon 12 will eliminate the BstNI site. The presence of two normal alleles results in all of the product being cleaved and the presence of one mutant and one normal allele will result in only half of the product cut. In the three panels each sample was run in duplicate, uncut and cut with BstNI. F1 is DNA from an untreated NFS/n X AKR F1 mouse, and MCA5 is a murine cell line known to harbor a mutant K-ras codon 12 allele. One lymphoma (24Ly) and one cell line (117; derived from a lung adenocarcinoma) display a mutated Ki-ras codon 12 allele; however, 24Ly was a passaged tumor and examination of the original tumor showed two normal alleles indicating that this mutation was acquired during passaging.
Figure 3B:
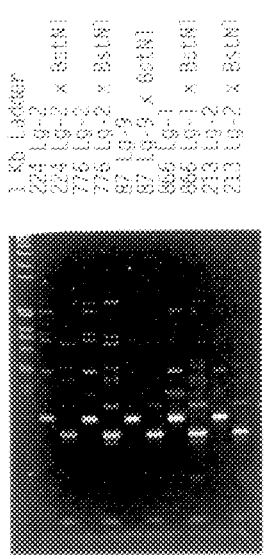
Figure 3C:
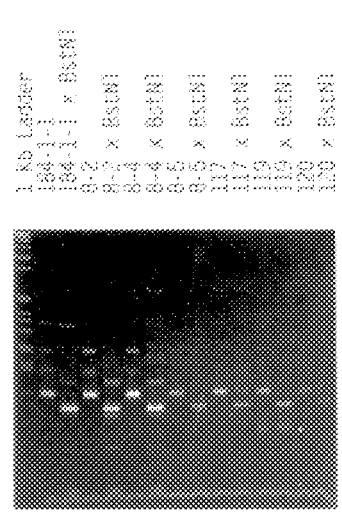

Northern blot analysis revealed elevated levels of c-raf-1, as compared to normal tissue, in every tumor examined (FIG. 2), and Western blot analysis showed that protein levels correlated with message levels (U. R. Rapp et al., in *Oncogenes and Cancer*, S. A. Aaronson et al., Eds. (Tokyo/VNU Scientific Press, Tokyo, 1987) pp. 55–74). In addition, in call lines derived from primary tumors, Raf-1 protein kinase activity was shown by immune-complex kinase assays to be constitutive. Further analysis of other oncogenes revealed no consistent pattern of expression except for ras and syc family genes. In the case of the mvc family, one member (either c-, N-, or L-mvc) was overexpressed but never more than one. For the ras genes, at least one member (Ki-, Ha-, or N-ras), and often more than one, was expressed at high levels when compared with the normal tissue. In addition all oncogenes examined via Northern analysis exhibited full length, normal sized transcripts.

ras genes were considered likely candidates for mutational activation since oncogenic forms of Ki-ras have previously been observed in lung tumors (S. Rodenhuis et al., *Am. Rev. Respir. Dis.* 142, S27–30; T. R. Devereux et al., *Carcinogenesis* 12, 299 (1991)) and ENU is a point mutagen (Singer, B. et al., 1983. *Molecular Biology of Mutagens and Carcinogens*, Plenum Press, New York). A systematic analysis of various ras codons known to be involved in oncogenic activation was therefore performed. Ha-, Ki-, and N-ras were examined at codons 12, 13, and 61 for potential mutations via RNAse protection assays (R. M. Myers et al., *Science* 230, 1242 (1985); E. Winter et al., *Proc. Natl. Acad. Sci. USA* 82, 7575 (1985)), PCR amplification followed by subsequent sequencing (F. Sanger et al., *J. Mol. Biol.* 13, 373 (1975)), and PCR amplification followed by diagnostic restriction digests (W. Jiang et al., *Oncogene* 4, 923 (1989)). PCR amplification creating diagnostic enzyme sites is a very efficient way of examining alleles for mutations at known sites and involves designing a PCR primer whose 3' end lies next to and produces a novel restriction site encompassing the codon of interest. Following amplification, PCR products from normal alleles will contain the new restriction site, while mutant alleles will not. Digestion of the product from tissue with two normal alleles results in all product being cut; however, if one allele contains a mutation, only half of the product will be digested. FIG. 3 shows the results of amplification and diagnostic digestion applied to Ki-ras codon 12 in several tumors and cell lines. The first panel is from a set of lymphomas. F1 is DNA from a normal untreated mouse and both alleles are cut by BstNl, indicating the presence of two normal alleles. MCA5 is a murine cell line known to contain a Ki-ras codon 12 mutation (L. F. Parada et al., *Mol. Cell. Biol.* 3, 2298 (1983)), and only the amplified normal allele is cleaved. Of the five tumors shown in the second panel, one shows a mutant Ki-ras allele. The next panel shows some of the lung tumors tested and none of them exhibit a mutant allele, and the final panel shows tumor derived cell lines. The first three are from lymphomas and the last three from lung adenocarcinomas. One lung tumor line (#117) has a Ki-ras 12 mutation that was not present in the primary tumor but came up upon transplantation. This analysis has been performed with Ki, Ha and N-ras genes at codons 12 and 61. Of all the tumors and cell lines examined by this method for mutations of the three ras genes at codons 12 and 61, the two shown here were the only ones detected. Examination of codon 13 was done by PCR amplification of genomic DNA surrounding codon 13 followed by cloning into KS+ (Stratagene) and double stranded sequencing. Table I summarizes the ras mutation data. The most notable point from this table is the conspicuous lack of ras mutations in these tumors. In fact the number of ras mutations is much lower than would be expected for a sampling of spontaneous tumors (S. Rodenhuis et al., *Am. Rev. Respir. Dis.* 142, S27–30; T. R. Devereux et al., *Carcinogenesis* 12, 299 (1991); J. L. Bos, *Cancer Res.* 49, 4682 (1989)). Having eliminated ras genes as playing a primary role in the genesis of these ENU induced tumors, c-raf-1 was investigated for possible small or point mutations.

TABLE I

Tumors and Cell Lines Positive for ras Mutations

|  | Codon 12 | | Codon 13 | | Codon 61 | |
| --- | --- | --- | --- | --- | --- | --- |
|  | Tumors | Cell Lines | Tumors | Cell Lines | Tumors | Cell Lines |
| Ha-ras | 0/10 | 0/6 | 0/6 | 0/2 | 0/10 | 0/6 |
| Ki/ras | 1*/10 | 1/6 | 0/6 | 0/2 | 0/6 | 0/2 |
| N-ras | 0/10 | 0/6 | 0/6 | 0/2 | 0/10 | 0/6 |

*This was a second passage tumor in which the original tumor did not contain a KI-ras mutation.

Table I: Summary of mutation analysis for Ha-, Ki-, and N-ras at codons 12, 13, and 61. Each box displays the number of mutations detected, over the number of tumors and tumor derived cell lines examined via RNAse protection, sequencing or diagnostic digestion, for each of the nine codons.

Example 3

Mutations in Raf-1

Figure 4:
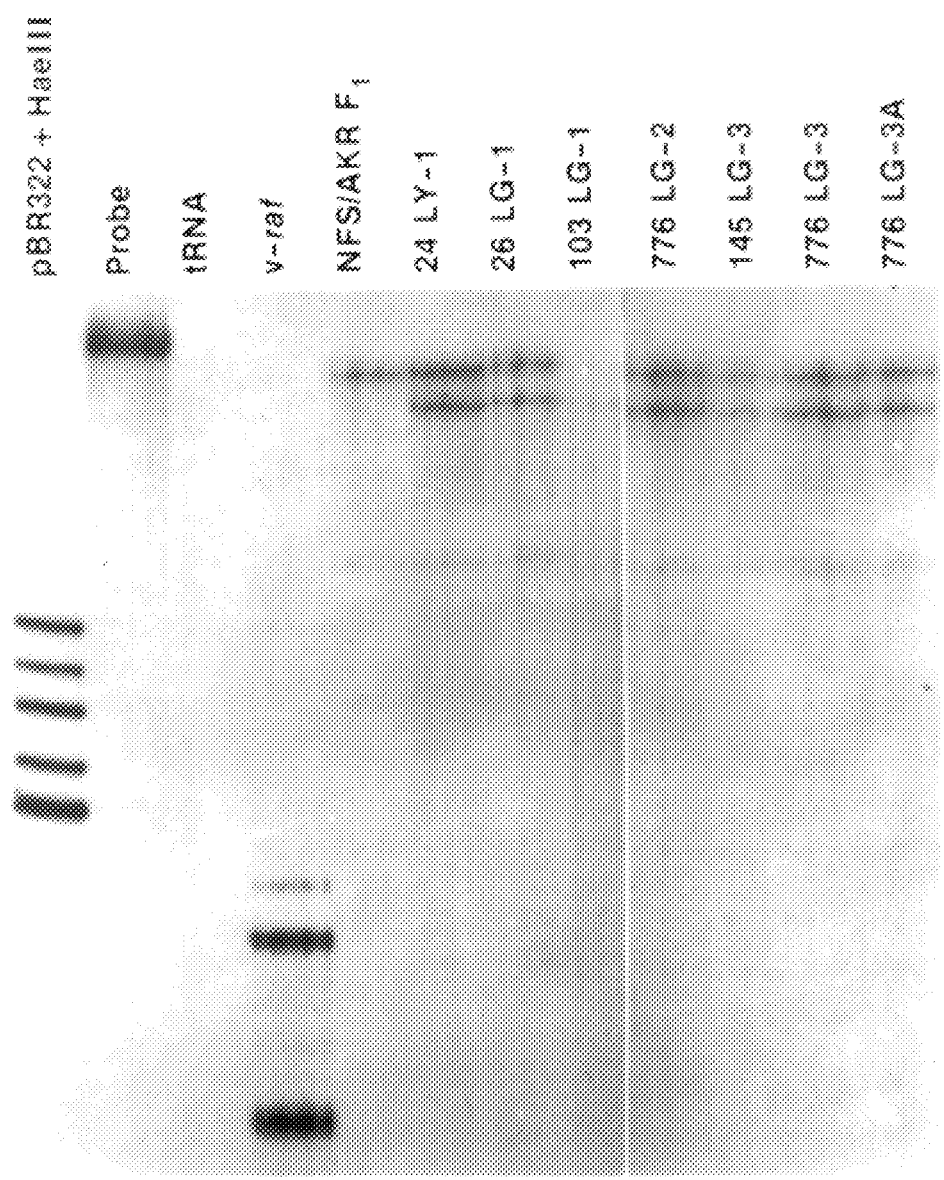
FIG. 4. c-raf-1 RNAse protection analysis of ENU induced tumors. The probe used was a $^{32}P$ labeled antisense transcript from the 3' non-coding region of a mouse c-raf-1 cDNA to the 3' most StuI site. Hybridization of this probe with normal RNA results in a protected fragment of 1.2 kb covering the region encoding the Raf-1 kinase domain. One $\mu g$ of poly(A)+ RNA from each tumor and 5 $\mu g$ of F1 RNA (in order to get comparable signals) was hybridized for 12 hours at 52° C. with 200,000 cpm of $^{32}P$ labeled mouse c-raf antisense transcript. Hybrids were then digested for 30 minutes with 25 $\mu g$ RNAse A and 33 units of RNAse T1 at room temperature. Digested hybrids were then incubated with 50 $\mu g$ of proteinase K, phenol/chloroform extracted, ethanol precipitated, and resuspended in loading dye containing 80% formamide. Samples were then run on 6% polyacrylamide denaturing sequencing gels at 65 watts. Gels were vacuum dried at 80 degrees C. and exposed to X-ray film. Probe is undigested probe alone; tRNA is probe hybridized to non-specific RNA; v-raf is probe hybridized to RNA from a v-raf transformed cell line and the bands detected represent single base mismatches between murine c-raf and v-raf; NFS/AKR F1 is probe hybridized with RNA from a normal (untreated) souse; 24 LY is probe hybridized with RNA from a lymphoma; and the remaining lanes are probe hybridized with RNA isolated from lung tumors.
Figure 5:
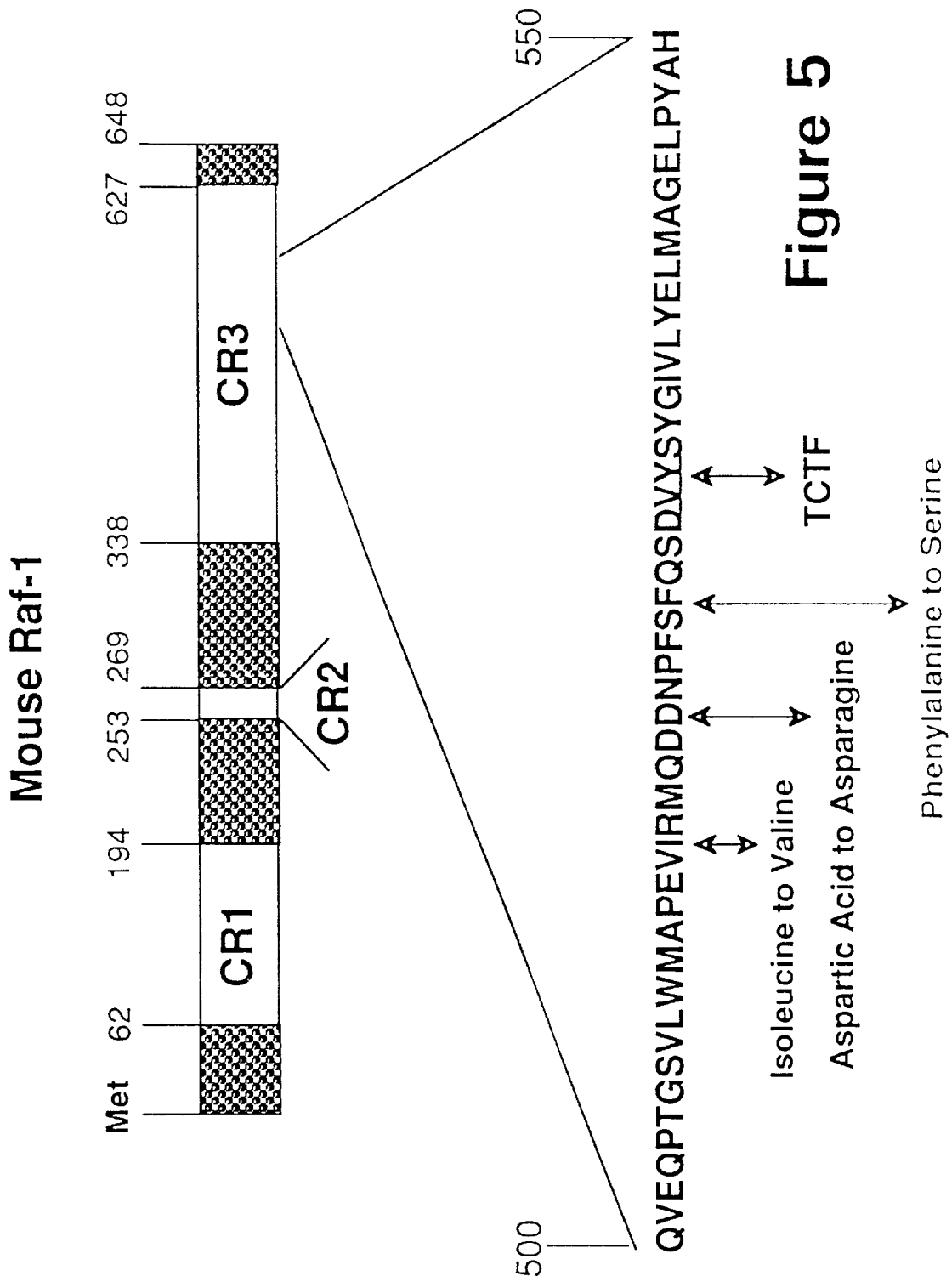
FIG. 5. Schematic of Raf-1 protein showing sites of ENU induced mutations. CR1, CR2, and CR3 represent conserved regions 1, 2 and 3. cDNAs were made from tumor derived poly(A)+ RNA using MoMuLV reverse transcriptase. Primers (MR1 sequence and MR2 sequence) encompassing a 435 base pair region c-raf were then used to amplify this region via PCR. The amplification mixture was then run on 1.7% agarose gels and the 435 bp product isolated. This isolated fragment was then treated with T4 polymerase and cloned into the HincII site of M13mp18 for sequencing. Another set of primers (EMR1 sequence and EMR2 sequence) was designed containing EcoRI sites at the termini and used to amplify a 609 base pair region (encompassing the original 435 base pair region). Isolated products from these reactions were then digested with EcoRI and cloned into the EcoRI site of KS. Sequencing reactions were carried out using the Sequenase kit (USB) according to the recommended protocols for single and double stranded sequencing. Sequencing reactions were run on 6% polyacrylamide denaturing gels at 65 watts. Gels were vacuum dried at 80 degrees C. and exposed to X-ray film. In each case a normal allele was also sequenced along with the mutant allele.

Since no point mutations had been described for raf genes in vivo, as had been for the ras genes (E. Santos et al., Science 223, 661 (1984); S. Rodenhuis, N. Engl. J. Med. 317, 929 (1987); M. Barbacid, Eur. J. Clin. Invest. 20, 225 (1990); F. Sanger et al., J. Mol. Biol. 13, 373 (1975)), point mutations were screened for using RNAse protection assays (R. M. Myers et al., Science 230, 1242 (1985); E. Winter et al., Proc. Natl. Acad. Sci. USA 82, 7575 (1985)). FIG. 4 shows a typical protection assay using a c-raf-1 probe. In this experiment the probe used covered the 3' end of raf-1 from the 3' most StuI site to the end of the coding sequence. The first lane is a marker (pBR322 digested with HaeIII), the second shows the probe alone undigested, the third lane shows the probe hybridized to unrelated RNA in this case tRNA, the fourth lane shows hybridization with v-raf transformed cells and the lower bands represent cleavage at points where the mouse c-raf-1 gene differs from v-raf. The fifth lane shows hybridization with RNA isolated from a normal lung of an untreated F1 mouse, the next lanes are RNA isolated from several tumors. In the case of the normal RNA, only one, fully protected, band is detected while in the case of the tumors two major bands are seen after digestion. 20 out of 20 tumors analyzed in this fashion showed this extra band. These data demonstrate the following major points: 1) there is a tumor specific alteration in c-raf-1 that results in a region of non-homology recognizable by either RNAse A or Tl; 2) The alterations are confined to the same region of one allele as two bands of equal size are present in the tumor lanes, and; 3) both alleles were expressed at comparable levels as both bands are of approximately equal intensity. In the assay shown 5 μg of poly(A)+ RNA was hybridized from normal tissue, and 1 μg was used from the tumors. This was necessary to get signals that could be compared on the same gel due to the overexpression of c-raf-1 in the tumors. By running these assays with various markers it was possible to estimate the approximate site of the alteration(s) to be in the vicinity of the exon 14/exon 15 junction. In order to define the precise genetic alteration or alterations, PCR primers were designed which would generate a 600 bp fragment encompassing this region. cDNAs from tumor derived RNA were then amplified and cloned into KS+ (Stratagene) for double stranded sequencing. The sequencing results from several tumors are shown in FIG. 5. The top portion of FIG. 5 presents a cartoon of the mouse Raf-1 protein. There are three conserved regions CR1, CR2 and CR3 with CR3 representing the kinase domain. The probe used in the RNAse protection assays covers the indicated area, and the PCR primers amplified the bracketed region. Sequencing through this area revealed a variety of mutations just downstream of the APE site. These mutants are shown in an expanded version at the bottom of FIG. 5 (See also SEQ ID NO:1 for normal mouse sequence and SEQ ID NO:2, 3, 4, and 5 for mutant sequences). These mutants were isolated from four separate tumors, and in each case a normal allele (SEQ ID NO:1) was also sequenced. Repeating the cDNA synthesis, PCR amplification, cloning and sequencing gives the same sequence and normal tissue shows no mutations demonstrating that these alterations are not artifactual. Sequence covering the amplified region has been examined and it is interesting that all of these changes occur within a very small region of the raf protein. In fact the region where these mutations occur overlaps an epitope shared by monoclonal antibodies generated against raf (W. Kolch et al., Oncogene 5, 713 (1990)), and computer modeling of the protein shows this to be a hydrophilic domain, the structure of which is predicted to be altered by these mutations. This indicates a biologically important region for the molecule and indeed the first of these mutation tested in NIH3T3 cell assays, after cloning into a retroviral expression vector (El-neo, (G. Heidecker et al., Mol. Cell. Biol. 10, 2503 (1990))), was found to be weakly transforming when driven by a Moloney LTR. The transformation efficiency was comparable to EC2, a previously characterized mutation of human c-raf-1 cDNA (G. Heidecker et al., Mol. Cell. Biol. 10, 2503 (1990); C. Wasylyk et al., Mol. Cell. Biol. 9, 2247 (1989)) and ~20 fold lower than the v-raf oncogene.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An isolated nucleic acid unique to c-raf-1 having a point mutation in the conserved region encoding amino acids 450 to 630 of SEQ ID NO:12.

2. The nucleic acid of claim 1 wherein the point mutation is in the conserved region encoding amino acids 500 to 550 of SEQ ID NO:12.

3. The nucleic acid of claim 1 wherein the point mutation is in the conserved region encoding amino acids 514 to 535 of SEQ ID NO:12.

4. The nucleic acid of claim 1 wherein the point mutation is in the conserved region encoding amino acid 533 of SEQ ID NO:12.

5. An isolated c-raf-1 protein having a point mutation in the conserved region corresponding to amino acids 450 to 630 of SEQ ID NO:12.

6. The protein of claim 5 wherein the point mutation is within amino acids 500 to 550 of SEQ ID NO:12.

7. The protein of claim 5 wherein the point mutation is within amino acids 514 to 535 of SEQ ID NO:12.

8. The protein of claim 5 wherein the point mutation is in amino acid 533 of SEQ ID NO:12.

* * * * *